(12) United States Patent
Conte et al.

(10) Patent No.: US 8,501,768 B2
(45) Date of Patent: Aug. 6, 2013

(54) HEXAHYDROCYCLOPENTAPYRROLONE, HEXAHYDROPYRROLOPYRROLONE, OCTAHYDROPYRROLOPYRIDINONE AND OCTAHYDROPYRIDINONE COMPOUNDS

(75) Inventors: Aurelia Conte, Shanghai (CN); Daniel Hunziker, Moehlin (CH); Werner Neidhart, Hagenthal-le-Bas (FR); Matthias Nettekoven, Grenzach-Wyhlen (DE); Tanja Schulz-Gasch, Ziefen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/463,863

(22) Filed: May 4, 2012

(65) Prior Publication Data
US 2012/0295934 A1  Nov. 22, 2012

(30) Foreign Application Priority Data
May 17, 2011 (EP) .................................. 11166437

(51) Int. Cl.
*C07D 209/52* (2006.01)
(52) U.S. Cl.
USPC .......................... 514/300; 514/323; 546/113
(58) Field of Classification Search
None
See application file for complete search history.

(56) References Cited

FOREIGN PATENT DOCUMENTS
WO     2010/108268     9/2010

OTHER PUBLICATIONS

Matsuki et al. Chem. Pharm. Bull. 1994, 42 (1), 9-18.*
Slee et al., Journal of Medicinal Chemistry (XP002295846), 46(7):1120-1122 (Feb. 28, 2003).
(International Search Report PCT/EP2012/058852 Aug. 2, 2012.

* cited by examiner

*Primary Examiner* — Jason M Nolan
*Assistant Examiner* — Ana Z Muresan

(57) ABSTRACT

The invention provides novel compounds having the general formula (I)

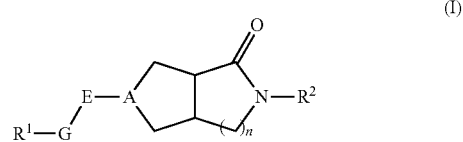

wherein $R^1$, $R^2$, A, E, G and n are as described herein, compositions including the compounds and methods of using the compounds. The compounds are useful as inhibitors of hormone sensitive lipase (HSL) and may be used for the treatment of diabetes, metabolic syndrome, dyslipidemia, atherosclerosis, obesity, cardiovascular diseases, myocardial dysfunction, inflammation, non-alcoholic fatty liver disease or non-alcoholic steatohepatitis.

33 Claims, No Drawings

HEXAHYDROCYCLOPENTAPYRROLONE, HEXAHYDROPYRROLOPYRROLONE, OCTAHYDROPYRROLOPYRIDINONE AND OCTAHYDROPYRIDINONE COMPOUNDS

PRIORITY TO RELATED APPLICATION(S)

This application claims the benefit of European Patent Application No. 11166437.1, filed May 17, 2011. The entire contents of the above-identified application are hereby incorporated by reference.

FIELD OF THE INVENTION

The present invention relates to organic compounds useful for therapy or prophylaxis in a mammal. In particular, the compounds are useful as inhibitors of hormone sensitive lipase (HSL) and may be used in the treatment of diabetes, metabolic syndrome, dyslipidemia, atherosclerosis, obesity, cardiovascular diseases, myocardial dysfunction, inflammation, non-alcoholic fatty liver disease or non-alcoholic steatohepatitis.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess. The release of free fatty acids (FFA) from TAG is stimulated by catecholamines and regulated by hormones such as insulin, glucagon and epinephrine. The most important enzyme in WAT believed responsible for hormone regulated hydrolysis of triglyceride is hormone sensitive lipase (HSL).

Dysregulation of adipocyte lipolysis, resulting in elevated circulating non-esterified fatty acids (NEFA) is associated with obesity and co-morbidities including the development of type 2 diabetes. Obese or insulin resistant subjects have increased visceral adipose tissue depots. These depots contain elevated levels of HSL protein and exhibit enhanced lipolytic activity as they are resistant to the insulin-mediated suppression of lipolysis. This results in increased plasma levels of free fatty acids (FFA), which further exacerbates insulin resistance due to the accumulation of triglycerides in tissues other than WAT such as liver, pancreas and muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

Elevated FFAs are also associated with increased cardiovascular risk, including atherosclerosis and myocardial dysfunction. Furthermore, high lipolytic activity and elevated FFAs lead to increased insulin resistance and hypertension in hypertensive rats. The FFA collect in the liver and lead to increased production of TAG, which are packaged into very low density lipoproteins (VLDL) which are secreted. Therefore, reducing the activity of HSL would decrease the release of FFA to the blood, thus limiting the supply of FFA to the liver for TAG synthesis. Thus, HSL inhibitors could have beneficial effects as treatment of non-alcoholic fatty liver disease (NAFLD) and non-alcoholic steatohepatitis (NASH).

SUMMARY OF THE INVENTION

The present invention relates to compounds according to formula (I),

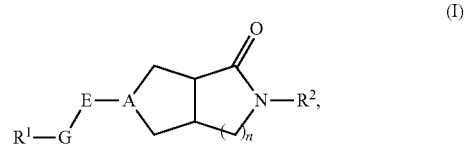

wherein:
$R^1$ is selected from the group consisting of alkyl, haloalkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, heteroaryl, substituted heteroaryl, heteroarylalkyl and substituted heteroarylalkyl, wherein substituted phenyl, substituted phenylalkyl, substituted phenoxyalkyl, substituted heteroaryl and substituted heteroarylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

$R^2$ is selected from the group consisting of phenyl, substituted phenyl, heteroaryl and substituted heteroaryl, wherein substituted phenyl and substituted heteroaryl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

$R^3$ is selected from the group consisting of hydrogen, hydroxy and alkoxy, wherein, when $R^3$ is hydroxy or alkoxy, E is —C($R^5R^6$)—;

$R^4$ is selected from the group consisting of hydrogen, alkyl and cycloalkyl;

$R^5$ is selected from the group consisting of hydrogen, alkyl and cycloalkyl;

$R^6$ is selected from the group consisting of hydrogen, alkyl and cycloalkyl;

n is 1 or 2;

A is —N or —C$R^3$;

E is a bond or —C($R^5R^6$)—; and

G is selected from the group consisting of —O—, —N$R^4$—, —CH(OH)—, —C(O)—, —C(O)O—, —C(O)N$R^4$—, —S(O)$_2$—, —S(O)$_2$N$R^4$— and a bond;

wherein, when both E and G are a bond, $R^1$ is directly attached to A.

The present invention also relates to salts and esters of the aforementioned compounds of formula (I).

Further objects of the present invention include the use of the compounds of formula (I) and their aforementioned salts and esters as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis and the use of the said compounds, salts or esters for the production of medicaments for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxymethyl, ethoxyethyl, methoxypropyl, ethoxypropyl, n-butoxymethyl and terbutoxymethyl. Particular alkoxyalkyl group include ethoxymethyl, n-butoxymethyl and terbutoxymethyl.

The term "alkoxyhaloalkyl" denotes an alkyl wherein at least one of the hydrogen atoms of the alkyl has been replaced by an alkoxy group and wherein at least one of the hydrogen atoms of the alkyl has been replaced by a halogen. Examples of alkoxyhaloalkyl include methoxytrifluoroethyl or methoxytrifluoropropyl.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, n-propyl, isopropyl, dimethylpropyl, n-butyl, iso-butyl, sec-butyl, tert-butyl, methylbutyl and dimethylbutyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl group is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "haloalkoxy" denotes an alkoxy group wherein at least one of the hydrogen atoms of the alkoxy group has been replaced by same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and trifluoroethoxy. More particular haloalkoxy groups are trifluoromethoxy and trifluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl group is 2,2,2-trifluoroethoxymethyl.

The term "haloalkyl" denotes an alkyl group wherein at least one of the hydrogen atoms of the alkyl group has been replaced by same or different halogen atoms. Examples of haloalkyl include fluoromethyl, difluoromethyl, trifluoromethyl, trifluoroethyl, trifluoromethylethyl and pentafluoroethyl. A particular haloalkyl groups is trifluoromethyl.

The term "halogen" and "halo" are used interchangeably herein and denote fluoro, chloro, bromo, or iodo. Particular halogens are chloro and fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl group is pyridinyl.

The term "heteroarylalkyl" denotes an alkyl group wherein at least one of the hydrogen atoms of the alkyl group has been replaced by a heteroaryl group. Example of heteroarylalkyl is pyridinylalkyl.

The term "hydroxy" denotes a —OH group.

The term "hydroxyhaloalkyl" denotes an alkyl wherein at least one of the hydrogen atoms of the alkyl has been replaced by a hydroxy group and wherein at least one of the hydrogen atoms of the alkyl has been replaced by a halogen. Examples of hydroxyhaloalkyl include hydroxytrifluoroethyl, hydroxytrifluoropropyl and hydroxyhexafluoropropyl.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl.

The term "phenoxy" denotes a group of the formula —O—R', wherein R' is a phenyl.

The term "phenoxyalkyl" denotes an alkyl group wherein at least one of the hydrogen atoms of the alkyl group has been replaced by a phenoxy group. Exemplary phenoxyalkyl groups include phenoxymethyl, phenoxyethyl and phenoxypropyl. Particular alkoxyalkyl group is phenoxymethyl.

The term "phenylalkyl" denotes an alkyl group wherein at least one of the hydrogen atoms of the alkyl group has been replaced by a phenyl. Examples of phenylalkyl include phenylmethyl, phenylethyl, phenylpropyl and phenylmethylpropyl. Particular phenylalkyl group is phenylmethyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and benzyl group (Bn).

The present invention relates to compounds according to formula (I),

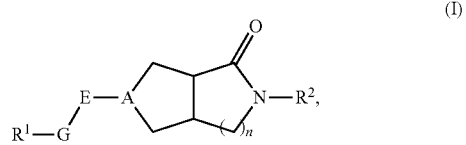

wherein:
$R^1$ is selected from the group consisting of alkyl, haloalkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, heteroaryl, substituted heteroaryl, heteroarylalkyl and substituted heteroarylalkyl, wherein substituted phenyl, substituted phenylalkyl, substituted phenoxyalkyl, substituted heteroaryl and substituted heteroarylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

$R^2$ is selected from the group consisting of phenyl, substituted phenyl, heteroaryl and substituted heteroaryl, wherein substituted phenyl and substituted heteroaryl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

$R^3$ is selected from the group consisting of hydrogen, hydroxy and alkoxy, wherein, when $R^3$ is hydroxy or alkoxy, E is $-C(R^5R^6)-$;

$R^4$ is selected from the group consisting of hydrogen, alkyl and cycloalkyl;

$R^5$ is selected from the group consisting of hydrogen, alkyl and cycloalkyl;

$R^6$ is selected from the group consisting of hydrogen, alkyl and cycloalkyl;

n is 1 or 2;

A is $-N$ or $-CR^3$;

E is a bond or $-C(R^5R^6)-$; and

G is selected from the group consisting of $-O-$, $-NR^4-$, $-CH(OH)-$, $-C(O)-$, $-C(O)O-$, $-C(O)NR^4-$, $-S(O)_2-$, $-S(O)_2NR^4-$ and a bond;

wherein, when both E and G are a bond, $R^1$ is directly attached to A.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are pharmaceutically acceptable salts or esters of the compounds according to formula (I), in particular pharmaceutically acceptable salts of compounds according to formula (I).

A further embodiment of the present invention are compounds according to formula (I) as described herein, wherein $R^1$ is selected from the group consisting of alkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, pyridinyl, substituted pyridinyl, pyridinylalkyl and substituted pyridinylalkyl, wherein substituted phenyl, substituted phenylalkyl, substituted phenoxyalkyl, substituted pyridinyl and substituted pyridinylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl.

A further particular embodiment of the present invention are compounds according to formula (I) as described herein, wherein $R^1$ is selected from the group consisting of alkyl, haloalkoxyalkyl, phenyl, substituted phenyl, phenylalkyl, substituted phenylalkyl or substituted pyridinyl, wherein substituted phenyl, substituted phenylalkyl and substituted pyridinyl are substituted with one to three substituents independently selected from the group consisting of alkyl, halogen, haloalkyl, hydroxy and haloalkoxy.

A particular embodiment of the present invention are compounds according to formula (I) as described herein, wherein $R^1$ is selected from the group consisting of alkyl, substituted phenyl and phenylalkyl, wherein substituted phenyl is substituted with one to three substituents independently selected from halogen and haloalkoxy.

In a further embodiment of the present invention are compounds according to formula (I) as described herein, wherein $R^1$ is alkyl.

Another further embodiment of the present invention are compounds according to formula (I) as described herein, wherein R¹ is phenylalkyl.

A particular embodiment of the present invention are compounds according to formula (I) as described herein, wherein R¹ is phenyl substituted with one to three substituents independently selected from halogen and haloalkoxy.

A further particular embodiment of the present invention are compounds according to formula (I) as described herein, wherein R¹ is phenyl substituted with one or two halogen.

Also an embodiment of the present invention are compounds according to formula (I) as described herein, wherein R¹ is 2-chlorophenyl or 2,4-dichlorophenyl.

Another embodiment of the present invention are compounds according to formula (I) as described herein, wherein R² is phenyl substituted with one substituent selected from alkyl and haloalkoxy.

The present invention also relates to compounds according to formula (I) as described herein, wherein R² is phenyl substituted with one haloalkoxy.

A further particular embodiment of the present invention are compounds according to formula (I) as described herein, wherein R² is 4-trifluoromethoxyphenyl.

A more particular embodiment of the present invention are compounds according to formula (I) as described herein, wherein A is —N.

Also an embodiment of the present invention are compounds according to formula (I) as described herein, wherein A is —CR³.

The present invention also relates to compounds according to formula (I) as described herein, wherein E is —C(R⁵R⁶)—.

Another embodiment of the present invention are compounds according to formula (I) as described herein, wherein E is a bond.

A further embodiment of the present invention are compounds according to formula (I) as described herein, wherein G is selected from the group consisting of —O—, —NR⁴—, —CH(OH)—, —C(O)—, —C(O)O—, —C(O)NR⁴—, —S(O)₂—, —S(O)₂NR⁴— and a bond.

A particular embodiment of the present invention are compounds according to formula (I) as described herein, wherein G is selected from the group consisting of O, —C(O)—, —CH(OH)— and —S(O)₂—.

Also an embodiment of the present invention are compounds according to formula (I) as described herein, wherein G is —C(O)— or —S(O)₂—.

Also an embodiment of the present invention are compounds according to formula (I) as described herein, wherein G is —S(O)₂—.

Another embodiment of the present invention are compounds according to formula (I) as described herein, wherein R³ is hydrogen or hydroxy, wherein, when R³ is hydroxy, E is —C(R⁵R⁶)—.

The present invention also relates to compounds according to formula (I) as described herein, wherein R³ is hydrogen.

Also an embodiment of the present invention are compounds according to formula (I) as described herein, wherein R⁴ is hydrogen.

Another embodiment of the present invention are compounds according to formula (I) as described herein, wherein R⁵ is hydrogen or alkyl.

Also an embodiment of the present invention are compounds according to formula (I) as described herein, wherein R⁵ is hydrogen.

A particular embodiment of the present invention are compounds according to formula (I) as described herein, wherein R⁶ is hydrogen.

A further embodiment of the present invention are compounds according to formula (I) as described herein, wherein both E and G are a bond and the compound is one of formula I(a).

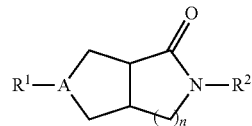

Also an embodiment of the present invention are compounds according to formula (I) as described herein, wherein n is 1.

A particular embodiment of the present invention are compounds according to formula (I) as described herein, wherein n is 2.

Particular examples of compounds of formula (I) as described herein are selected from the group consisting of:
(3aR,7aS)-4-oxo-5-(4-trifluoromethoxy-phenyl)-octahydro-pyrrolo[3,4-c]pyridine-2-carboxylic acid tert-butyl ester;
(3aS,7aR)-2-Phenylacetyl-5-(4-trifluoromethoxy-phenyl)-octahydro-pyrrolo[3,4-c]pyridin-4-one;
(3aS,7aR)-2-(4-Fluoro-benzoyl)-5-(4-trifluoromethoxy-phenyl)-octahydro-pyrrolo[3,4-c]pyridin-4-one;
(3aS,7aR)-2-(3-Methyl-butyryl)-5-(4-trifluoromethoxy-phenyl)-octahydro-pyrrolo[3,4-c]pyridin-4-one;
(3aS,7aR)-4-Oxo-5-(4-trifluoromethoxy-phenyl)-octahydro-pyrrolo[3,4-c]pyridine-2-carboxylic acid (4-trifluoromethoxy-phenyl)-amide;
(3aS,7aR)-2-(4-Fluoro-benzyl)-5-(4-trifluoromethoxy-phenyl)-octahydro-pyrrolo[3,4-c]pyridin-4-one;
(3aS,7aR)-2-(2-Chloro-benzoyl)-5-(4-trifluoromethoxy-phenyl)-octahydro-pyrrolo[3,4-c]pyridin-4-one;
(3aS,7aR)-2-(4-Isopropyl-benzoyl)-5-(4-trifluoromethoxy-phenyl)-octahydro-pyrrolo[3,4-c]pyridin-4-one;
(3aS,7aR)-2-(3-Methyl-butane-1-sulfonyl)-5-(4-trifluoromethoxy-phenyl)-octahydro-pyrrolo[3,4-c]pyridin-4-one;
(3aS,7aR)-2-(2-Methyl-propane-1-sulfonyl)-5-(4-trifluoromethoxy-phenyl)-octahydro-pyrrolo[3,4-c]pyridin-4-one;
(3aS,7aR)-2-(2-Chloro-benzenesulfonyl)-5-(4-trifluoromethoxy-phenyl)-octahydro-pyrrolo[3,4-c]pyridin-4-one;
(3aS,7aR)-2-(4-Fluoro-benzenesulfonyl)-5-(4-trifluoromethoxy-phenyl)-octahydro-pyrrolo[3,4-c]pyridin-4-one;
(3aS,7aR)-2-Phenylmethanesulfonyl-5-(4-trifluoromethoxy-phenyl)-octahydro-pyrrolo[3,4-c]pyridin-4-one;
(3aS,7aR)-4-Oxo-5-(4-trifluoromethoxy-phenyl)-octahydro-pyrrolo[3,4-c]pyridine-2-carboxylic acid (4-fluoro-phenyl)-amide;
(3aR,7aS)-2-(2-Chloro-pyridine-3-sulfonyl)-5-[4-(2,2,2-trifluoro-ethoxy)-phenyl]-octahydro-pyrrolo[3,4-c]pyridin-4-one;

(3aR,7aS)-2-Benzenesulfonyl-5-[4-(2,2,2-trifluoro-ethoxy)-phenyl]-octahydro-pyrrolo[3,4-c]pyridin-4-one;
(3aR,7aS)-5-[4-(2,2,2-Trifluoro-ethoxy)-phenyl]-2-(2-trifluoromethoxy-benzenesulfonyl)-octahydro-pyrrolo[3,4-c]pyridin-4-one;
(3aR,7aS)-2-(2-p-Tolyl-acetyl)-5-[4-(2,2,2-trifluoro-ethoxy)-phenyl]-octahydro-pyrrolo[3,4-c]pyridin-4-one;
(3aR,7aS)-2-[2-(4-Fluoro-phenyl)-acetyl]-5-[4-(2,2,2-trifluoro-ethoxy)-phenyl]-octahydro-pyrrolo[3,4-c]pyridin-4-one;
(3aR,7aS)-5-[4-(2,2,2-Trifluoro-ethoxy)-phenyl]-2-(2-trifluoromethyl-benzenesulfonyl)-octahydro-pyrrolo[3,4-c]pyridin-4-one;
(3aR,7aS)-2-Phenylacetyl-5-[4-(2,2,2-trifluoro-ethoxy)-phenyl]-octahydro-pyrrolo[3,4-c]pyridin-4-one;
(3aR,7aS)-2-(3,3-Dimethyl-butyryl)-5-[4-(2,2,2-trifluoro-ethoxy)-phenyl]-octahydro-pyrrolo[3,4-c]pyridin-4-one;
(3aR,7aS)-2-(2-Chloro-benzenesulfonyl)-5-[4-(2,2,2-trifluoro-ethoxy)-phenyl]-octahydro-pyrrolo[3,4-c]pyridin-4-one;
N-(4-Fluoro-phenyl)-3-methyl-2-{(3aR,7aS)-4-oxo-5-[4-(2,2,2-trifluoro-ethoxy)-phenyl]-octahydro-pyrrolo[3,4-c]pyridin-2-yl}-butyramide;
(3aR,7aS)-4-oxo-5-[4-(2,2,2-trifluoro-ethoxy)-phenyl]-octahydro-pyrrolo[3,4-c]pyridine-2-carboxylic acid tert-butyl ester;
(3aR,7aS)-2-[2-(2,4-Dichloro-phenyl)-2-hydroxy-ethyl]-5-[4-(2,2,2-trifluoro-ethoxy)-phenyl]-octahydro-pyrrolo[3,4-c]pyridin-4-one;
(3aR,7aS)-2-(2-Hydroxy-phenyl)-5-[4-(2,2,2-trifluoro-ethoxy)-phenyl]-octahydro-pyrrolo[3,4-c]pyridin-4-one;
(3aS,6aS)-4-oxo-5-(4-trifluoromethoxy-phenyl)-hexahydro-pyrrolo[3,4-c]pyrrole-2-carboxylic acid (4-trifluoromethoxy-phenyl)-amide;
(3aS,6aS)-5-(4-Ethyl-phenyl)-4-oxo-hexahydro-pyrrolo[3,4-c]pyrrole-2-carboxylic acid (4-trifluoromethoxy-phenyl)-amide;
(3aR,6aS)-5-Hydroxy-5-propyl-2-(4-trifluoromethoxy-phenyl)-hexahydro-cyclopenta[c]pyrrol-1-one;
(3aR,5S,6aS)-5-Hydroxy-5-(2,2,2-trifluoro-ethoxymethyl)-2-(4-trifluoromethoxy-phenyl)-hexahydro-cyclopenta[c]pyrrol-1-one;
(3aR,6aS)-5-Hydroxy-5-phenylaminomethyl-2-(4-trifluoromethoxy-phenyl)-hexahydro-cyclopenta[c]pyrrol-1-one;

2-Chloro-N-[(3aR,6aS)-1-oxo-2-(4-trifluoromethoxy-phenyl)-octahydro-cyclopenta[c]pyrrol-5-yl]-benzenesulfonamide;
(3aR,5S,6aS)-5-Hydroxy-5-phenoxymethyl-2-(4-trifluoromethoxy-phenyl)-hexahydro-cyclopenta[c]pyrrol-1-one;
(3aR,5S,6aS)-5-Hydroxy-5-propoxymethyl-2-(4-trifluoromethoxy-phenyl)-hexahydro-cyclopenta[c]pyrrol-1-one;
(3aR,5S,6aS)-5-Butoxymethyl-5-hydroxy-2-(4-trifluoromethoxy-phenyl)-hexahydro-cyclopenta[c]pyrrol-1-one;
and pharmaceutically acceptable salts thereof.

Further particular examples of compounds of formula (I) as described herein are selected from the group consisting of:
(3aS,7aR)-2-Phenylacetyl-5-(4-trifluoromethoxy-phenyl)-octahydro-pyrrolo[3,4-c]pyridin-4-one;
(3aS,7aR)-2-(2-Chloro-benzenesulfonyl)-5-(4-trifluoromethoxy-phenyl)-octahydro-pyrrolo[3,4-c]pyridin-4-one;
(3aR,7aS)-5-[4-(2,2,2-Trifluoro-ethoxy)-phenyl]-2-(2-trifluoromethoxy-benzenesulfonyl)-octahydro-pyrrolo[3,4-c]pyridin-4-one;
(3aR,7aS)-2-[2-(2,4-Dichloro-phenyl)-2-hydroxy-ethyl]-5-[4-(2,2,2-trifluoro-ethoxy)-phenyl]-octahydro-pyrrolo[3,4-c]pyridin-4-one;
(3aR,5S,6aS)-5-Butoxymethyl-5-hydroxy-2-(4-trifluoromethoxy-phenyl)-hexahydro-cyclopenta[c]pyrrol-1-one;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In more detail, the compounds of formula I can be manufactured by the methods given below, by the methods given in the examples or by analogous methods. Appropriate reaction conditions for the individual reaction steps are known to a person skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

Scheme 1

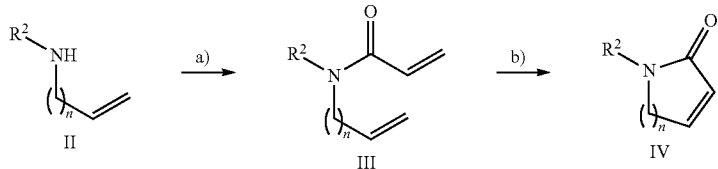

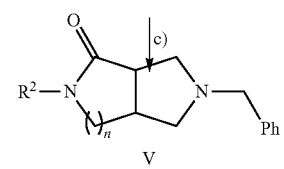

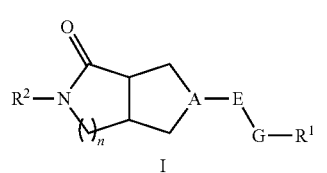 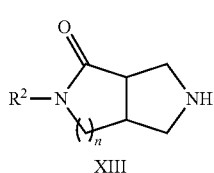 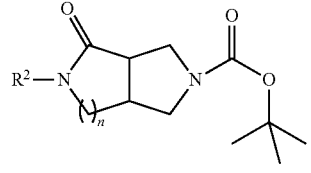

a) Derivatives II are either commercially available or can be synthesized conveniently from the respective compounds of formula R²—NH₂ and 3-bromopropene or 4-bromobut-1-ene to afford the derivatives II. These can be reacted with acrolyl chloride to yield compounds III.

b) A ring-closing metathesis reaction of III under transition metal catalysis yields unsaturated lactams IV.

c) Lactams IV can be reacted in a [3+2] cycloaddition with N-benzyl(methoxy)-N-((trimethylsilyl)methyl)methanamine to yield protected bi-cycles V.

d) Protecting group manipulation in V yielded derivatives VI which can already be final products. Nevertheless, the Boc-protecting group in VI can be cleaved under acidic conditions to yield the free amine XIII (step e) which can be derivatised to access final derivatives I (step n).

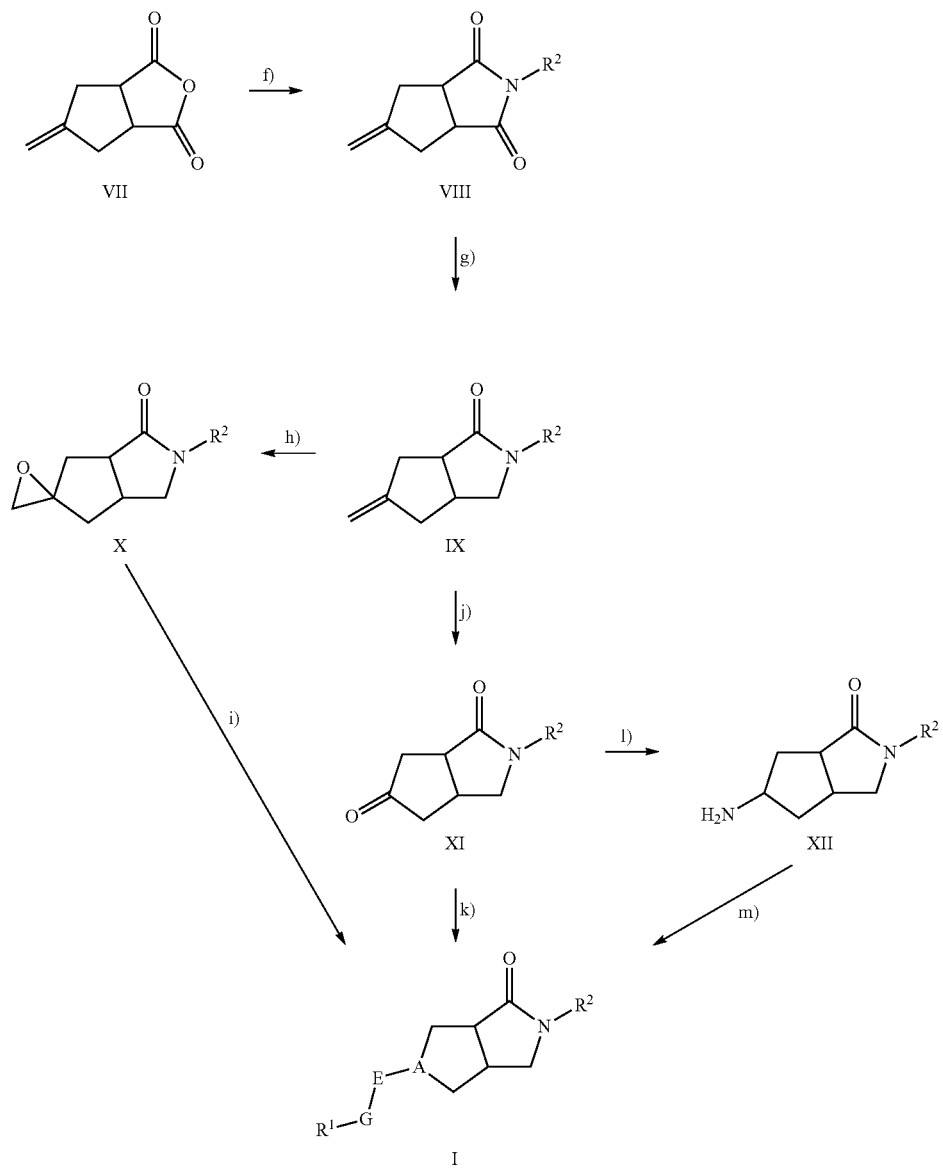

Scheme 2 f) 5-Methylene-tetrahydro-cyclopenta[c]furan-1,3-dione VII is commercially available and can be reacted with compounds of formula $R^2-NH_2$ under elevated temperatures to access diones VIII.

g) Diones VIII are conveniently reduced in a two-step procedure with $CeCl_3.7H_2O$, $NaBH_4$, $NaCNBH_3$ to access bi-cyclic lactam IX.

h) Epoxidation of IX is conveniently done with mCPBA to access X.

i) Opening of the epoxide X with various nucleophiles is done in the presence of a base to yield final compounds I, wherein A is $-CR^3$, $R^3$ is hydroxy, n is 1, E is $-C(R^5R^6)-$, $R^5$ and $R^6$ are hydrogen and G is a bond.

j) Conversion of the double bond in IX to access ketone XI can conveniently be done with ozonolysis.

k) Addition of e.g. Grignard reagents to ketone XI yielded the final tertiary alcohols I, wherein A is $-CR^3$, $R^3$ is hydroxy, n is 1, E is $-C(R^5R^6)-$, $R^5$ and $R^6$ are hydrogen and G is a bond.

l) The ketone XI can be converted by reductive amination with benzylamine to an amine derivative which under protecting group manipulation can be transformed to the respective Boc-derivative from which the protecting group can be cleaved under acidic conditions to access amine derivative XII.

m) Amine derivative XII can be derivatized to yield final derivatives I, wherein A is $-CR^3$, $R^3$ is hydrogen, n is 1, E is a bond and G is $-NR^4$, $-C(O)NR^4-$ or $-S(O)_2NR^4-$.

Also an embodiment of the present invention is a process to prepare a compound of formula (I) as defined above comprising the reaction of a) a compound of formula (XIII);

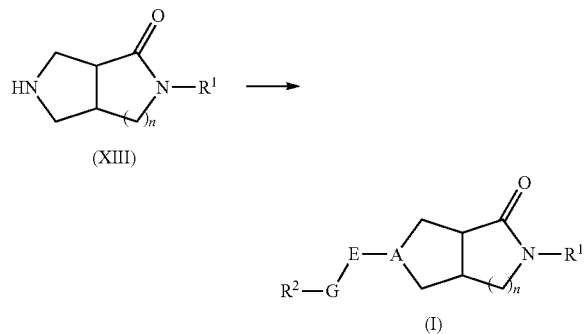

In particular in presence or not of a base, particularly diispropoylethylamine and triethylamine, in a solvent, particularly $CH_2Cl_2$, at a temperature comprised between RT and reflux, wherein R', $R^2$, E, G and n are as defined herein and A is —N.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

Also an object of the present invention is the use of a compound according to formula (I) as described herein for the treatment or prophylaxis of illnesses which are caused by disorders associated with the enzyme hormone-sensitive lipase.

The present invention relates to the use of a compound according to formula (I) as described above for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis The present invention particularly relates to the use of a compound according to formula (I) as described above for the treatment or prophylaxis of diabetes, metabolic syndrome, dyslipidemia, atherosclerosis or obesity.

A particular embodiment of the present invention is the use of a compound according to formula (I) as described above for the treatment or prophylaxis of diabetes.

A further particular embodiment of the present invention is the use of a compound according to formula (I) as described above for the treatment or prophylaxis of diabetes Type II.

Also an embodiment of the present invention is the use of a compound according to formula (I) as described above for the treatment or prophylaxis of cardiovascular diseases, myocardial dysfunction, inflammation, non-alcoholic fatty liver disease or non-alcoholic steatohepatitis.

A particular embodiment of the present invention is the use of a compound according to formula (I) as described above for the treatment or prophylaxis of non-alcoholic fatty liver disease or non-alcoholic steatohepatitis.

The present invention also relates to the use of a compound according to formula (I) as described above for the preparation of a medicament for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis.

The present invention particularly relates to the use of a compound according to formula (I) as described above for the preparation of a medicament for the treatment or prophylaxis of diabetes, metabolic syndrome, dyslipidemia, atherosclerosis or obesity.

A particular embodiment of the present invention is the use of a compound according to formula (I) as described above for the preparation of medicaments for the treatment or prophylaxis of diabetes.

A further particular embodiment of the present invention is the use of a compound according to formula (I) as described above for the preparation of medicaments for the treatment or prophylaxis of diabetes Type II.

Also an embodiment of the present invention is the use of a compound according to formula (I) as described above for the preparation of a medicament for the treatment or prophylaxis of cardiovascular diseases, myocardial dysfunction, inflammation, non-alcoholic fatty liver disease or non-alcoholic steatohepatitis.

A particular embodiment of the present invention is the use of a compound according to formula (I) as described above for the preparation of a medicament for the treatment or prophylaxis of non-alcoholic fatty liver disease or non-alcoholic steatohepatitis.

The present invention particularly relates to a compound according to formula (I) as described above for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis.

A particular embodiment of the present invention is a compound according to formula (I) as described above for the treatment or prophylaxis of diabetes, metabolic syndrome, dyslipidemia, atherosclerosis or obesity.

A further particular embodiment of the present invention is a compound according to formula (I) as described above for the treatment or prophylaxis of diabetes.

Also a further particular embodiment of the present invention is a compound according to formula (I) as described above for the treatment or prophylaxis of diabetes Type II.

Also a particular embodiment of the present invention is a compound according to formula (I) as described above for the treatment or prophylaxis of cardiovascular diseases, myocardial dysfunction, inflammation, non-alcoholic fatty liver disease or non-alcoholic steatohepatitis.

A further particular embodiment of the present invention is a compound according to formula (I) as described above for the treatment or prophylaxis of non-alcoholic fatty liver disease or non-alcoholic steatohepatitis.

Also an object of the invention is a method for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis, which method comprises administering an effective amount of a compound according to formula (I) as described above.

Also a particular object of the invention is a method for the treatment or prophylaxis of diabetes, metabolic syndrome, dyslipidemia, atherosclerosis or obesity, which method comprises administering an effective amount of a compound according to formula (I) as described above.

A particular embodiment of the present invention is a method for the treatment or prophylaxis of diabetes, which method comprises administering an effective amount of a compound according to formula (I) as described above.

A further particular embodiment of the present invention is a method for the treatment or prophylaxis of diabetes Type II, which method comprises administering an effective amount of a compound according to formula (I) as described above.

Also an embodiment of the present invention is a method for the treatment or prophylaxis of cardiovascular diseases, myocardial dysfunction, inflammation, non-alcoholic fatty liver disease or non-alcoholic steatohepatitis, which method comprises administering an effective amount of a compound according to formula (I) as described above.

Also a further embodiment of the present invention is a method for the treatment or prophylaxis of non-alcoholic fatty liver disease or non-alcoholic steatohepatitis, which method comprises administering an effective amount of a compound according to formula (I) as described above.

A further object of the present invention comprises a compound according to formula (I) as described herein, when manufactured according to any one of the described processes.

Assay Procedures

Production of Human full length Hormone Sensitive Lipase-His[6]:
1) Cloning: cDNA was prepared from commercial human brain polyA+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the E. coli strain DH10BAC. Resulting bacmid DNA was used to generate a titered baculovirus stock for protein generation. The sequence of the encoded HSL conforms to Swissprot entry Q05469, with the additional C-terminal His6-tag.
2) Protein purification: Culture: 5.5 L, High 5 cells expressing human full length HSL-His[6], 48 hr., containing 25 µM E-64. Cell count: $1.78 \times 10^{10}$ cells/ml, 90% viable. Cells were thawed. On ice, cells were suspended in Base Buffer containing 10% glycerol, 25 mM Tris-Cl, 300 mM NaCl, 10 mM imidazole, 10 mM 2-mercaptoethanol, 2 µg pepstatin/ml, 2 µg leupeptin/ml, 2 µg antipain/ml, pH 8.0 at 4° C. in a final volume of 475 ml with $3.75 \times 10^7$ cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 µm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 µm membrane disposable filter unit (Millipore SCGP UO2 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 µm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes).

3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Example | HSL hum IC50 (uM) |
|---|---|
| 1 | 0.17 |
| 2 | 0.0495 |
| 3 | 0.354 |
| 4 | 0.71 |
| 5 | 0.136 |
| 6 | 0.359 |
| 7 | 0.311 |
| 8 | 0.259 |
| 9 | 0.438 |
| 10 | 0.956 |
| 11 | 0.0501 |
| 12 | 0.38 |
| 13 | 0.174 |
| 14 | 0.845 |
| 15 | 0.727 |
| 16 | 0.953 |
| 17 | 0.0512 |
| 18 | 0.244 |
| 19 | 0.867 |
| 20 | 0.268 |
| 21 | 0.327 |
| 22 | 0.701 |
| 23 | 0.161 |
| 24 | 0.153 |
| 25 | 0.334 |
| 26 | 0.033 |
| 27 | 0.7 |
| 28 | 0.896 |
| 29 | 0.637 |
| 30 | 0.502 |
| 31 | 0.443 |
| 32 | 0.279 |
| 33 | 0.0965 |
| 34 | 0.482 |
| 35 | 0.554 |
| 36 | 0.139 |

Compounds of formula (I) and their pharmaceutically acceptable salts or esters thereof as described above have $IC_{50}$ values between 0.0001 uM and 1000 uM, particular compounds have $IC_{50}$ values between 0.001 uM and 500 uM, further particular compounds have $IC_{50}$ values between 0.001 uM and 5 uM. These results have been obtained by using the foregoing HSL enzyme inhibition assay (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

4-oxo-5-(4-trifluoromethoxy-phenyl)-octahydro-pyrrolo[3,4-c]pyridine-2-carboxylic acid tert-butyl ester

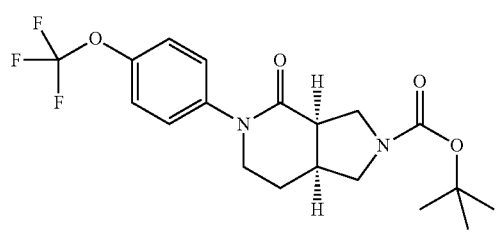 [SMILES: CC(C)(C)OC(=O)N1C[C@H]2CCN(c3ccc(OC(F)(F)F)cc3)C(=O)[C@H]2C1]

a) But-3-enyl-(4-trifluoromethoxy-phenyl)-amine

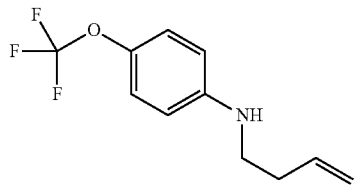 [SMILES: C=CCCNc1ccc(OC(F)(F)F)cc1]

4-Trifluoromethoxy-phenylamine (2.5 g, 14 mmol), 4-bromobut-1-ene (2.0 g, 14 mmol) and Cs$_2$CO$_3$ (1.4 g, 4.2 mmol) were mixed together, and the mixture was stirred at ambient temperature for 7 days. The title compound (0.2 g, 6.1%) was obtained by silica gel column chromatography (eluting with petroleum ether/ethyl acetate=10/1). $^1$H NMR (300 MHz, CDCl$_3$): δ 7.12-7.02 (m, 2H), 6.58-6.53 (m, 2H), 5.80-5.46 (m, 1H), 5.20-5.11 (m, 2H), 3.17 (t, 2H, J=6.6 Hz), 2.43-2.35 (m, 2H). LC-MS: [M+1]$^+$ 232.2.

b) N-But-3-enyl-N-(4-trifluoromethoxy-phenyl)-acrylamide

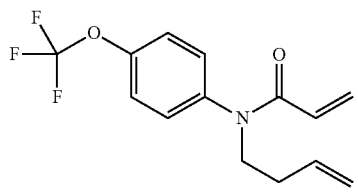 [SMILES: C=CCCN(C(=O)C=C)c1ccc(OC(F)(F)F)cc1]

Acryloyl chloride (0.7 g, 7.8 mmol) was added dropwise to a solution of But-3-enyl-(4-trifluoromethoxy-phenyl)-amine (1.2 g, 5.2 mmol) and Et$_3$N (1.1 g, 10.4 mmol). The mixture was stirred at ambient temperature overnight. The mixture was extracted with DCM, washed with brine, dried over anhydrous Na$_2$SO$_4$. The solvent was removed by reduced pressure and the residue was purified by silica gel column chromatography (eluting with petroleum ether/ethyl acetate=10/1) to give N-But-3-enyl-N-(4-trifluoromethoxy-phenyl)-acrylamide (0.8 g, 54%). $^1$H NMR (300 MHz, CDCl$_3$): δ 7.35-7.18 (m, 4H), 6.38-6.35 (m, 1H), 5.96-5.93 (m, 1H), 5.78-5.74 (m, 1H), 5.68-5.64 (m, 1H), 5.08-5.01 (m, 2H), 3.84 (t, 2H, J=7.5 Hz), 2.31-2.27 (m, 2H). LC-MS: [M+1]$^+$ 286.1.

c) 1-(4-Trifluoromethoxy-phenyl)-5,6-dihydro-1H-pyridin-2-one

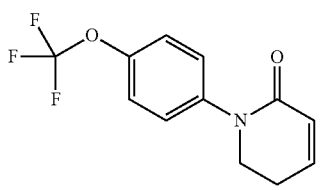 [SMILES: O=C1C=CCCN1c1ccc(OC(F)(F)F)cc1]

To N-But-3-enyl-N-(4-trifluoromethoxy-phenyl)-acrylamide (0.8 g, 2.6 mmol) in DCM (20 mL) was added Grubbs catalyst (0.12 g, 0.14 mmol) and the mixture was heated to 45° C. overnight. The solvent was removed by reduced pressure and the residue was purified by silica gel column chromatography (eluting with petroleum ether/ethyl acetate=10/1) to afford the title compound (0.6 g, 82%). $^1$H NMR (300 MHz, CDCl$_3$): δ 7.35-7.21 (m, 4H), 6.74-6.71 (m, 1H), 6.07-6.05 (m, 1H), 3.87-3.82 (m, 2H), 2.57-2.51 (m, 2H); LC-MS: [M+1]$^+$ 258.1.

d) 2-Benzyl-5-(4-trifluoromethoxy-phenyl)-octahydro-pyrrolo[3,4-c]pyridin-4-one

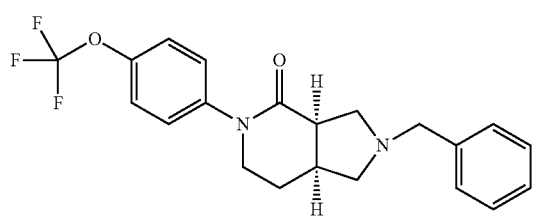 [SMILES: O=C1[C@H]2CN(Cc3ccccc3)C[C@H]2CCN1c1ccc(OC(F)(F)F)cc1]

To N-benzyl(methoxy)-N-((trimethylsilyl)methyl)methanamine (1.7 g, 7.0 mmol) and 1-(4-trifluoromethoxy-phenyl)-5,6-dihydro-1H-pyridin-2-one (0.6 g, 2.3 mmol) in DCM (30 mL) was added a solution of trifluoroacetic acid (0.026 g, 0.23 mmol) in DCM (10 mL) at 4° C. After the mixture was stirred at 50° C. for 3 h, the solution was washed with saturated sodium bicarbonate and brine, then dried over anhydrous Na$_2$SO$_4$. After removal of the DCM, the residue was purified by column chromatography on silica gel with petroleum ether/ethyl acetate P (10:1 to 5:1) to yield the title compound (0.19 g, 21%). $^1$H NMR (300 MHz, CDCl$_3$): δ 7.34-7.20 (m, 9H), 3.77-3.55 (m, 4H), 3.18-3.01 (m, 2H), 2.93-3.83 (m, 3H), 2.43-2.41 (m, 1H), 2.07-2.05 (m, 1H), 1.80-1.75 (m, 1H); LC-MS: [M+1]$^+$ 391.1.

e) 4-oxo-5-(4-trifluoromethoxy-phenyl)-octahydro-pyrrolo[3,4-c]pyridine-2-carboxylic acid tert-butyl ester The suspension of 2-Benzyl-5-(4-trifluoromethoxy-phenyl)-octahydro-pyrrolo[3,4-c]pyridin-4-one (1.0 g, 2.56 mmol), 10% Pd/C (0.5 g, 0.1 (w/w)) and di-tert-butyl dicarbonate (0.8 g, 3.8 mmol) in methanol (50 mL) was stirred under hydrogen atmosphere at room temperature for 3 h. The catalyst was filtered off. The filtrate was concentrated and the residue was purified by column chromatography on silica gel with petroleum ether/ethyl acetate (10:1 to 5:1) to yield the title compound (0.9 g, 90%). $^1$H NMR (300 MHz, CDCl$_3$): δ 7.38-7.20 (m, 4H), 3.89-3.59 (m, 5H), 3.40-3.37 (m, 1H), 3.20-3.15 (m, 1H), 2.72-2.70 (m, 1H), 2.07-1.89 (m, 2H), 1.52 (s, 9H); LC-MS: [M+23]$^1$ 422.9.

Example 2

2-Phenylacetyl-5-(4-trifluoromethoxy-phenyl)-octahydro-pyrrolo[3,4-c]pyridin-4-one

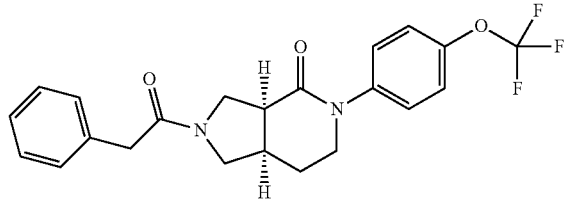 [SMILES: O=C(Cc1ccccc1)N1C[C@@H]2CCN(c3ccc(OC(F)(F)F)cc3)C(=O)[C@@H]2C1]

a) 5-(4-Trifluoromethoxy-phenyl)-octahydro-pyrrolo[3,4-c]pyridin-4-one, hydrochloride

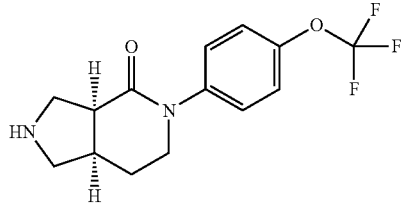 [SMILES: O=C1[C@@H]2CNC[C@@H]2CCN1c1ccc(OC(F)(F)F)cc1]

4-oxo-5-(4-trifluoromethoxy-phenyl)-octahydro-pyrrolo[3,4-c]pyridine-2-carboxylic acid tert-butyl ester (900 mg, 2.25 mmol) was added to a solution of saturated hydrochloride in ethyl acetate (4 mL). The reaction mixture was stirred at ambient temperature overnight. The solvent was removed under reduced pressure, then the crude product (800 mg) was obtained which was used without further purification. $^1$H NMR (300 MHz, d6-DMSO): δ 7.51-7.38 (m, 4H), 3.79-3.25 (m, 6H), 3.04-3.01 (m, 1H), 2.84-2.81 (m, 1H), 2.06-2.03 (m, 1H), 1.82-1.80 (m, 1H); LC-MS: [M+1]+ 302.7.

b) 2-Phenylacetyl-5-(4-trifluoromethoxy-phenyl)-octahydro-pyrrolo[3,4-c]pyridin-4-one 5-(4-Trifluoromethoxy-phenyl)-octahydro-pyrrolo[3,4-c]pyridin-4-one, hydrochloride (80 mg, 0.24 mmol), 2-phenylacetyl chloride (74 mg, 0.48 mmol) and Et$_3$N (0.12 g, 1.2 mmol) were added to DCM (10 mL), and the mixture was stirred for 12 h at ambient temperature. The product (45 mg, 46%) was obtained by prep-TLC (eluting with DCM/MeOH=25/1). $^1$H NMR (300 MHz, CDCl$_3$): δ 7.34-7.23 (m, 9H), 3.90-3.54 (m, 7H), 3.23-3.20 (m, 2H), 2.78-2.75 (m, 1H), 2.07-2.02 (m, 1H), 1.83 (bs, 1H); LC-MS: [M+1]$^+$ 418.7.

Example 3

2-(4-Fluoro-benzoyl)-5-(4-trifluoromethoxy-phenyl)-octahydro-pyrrolo[3,4-c]pyridin-4-one

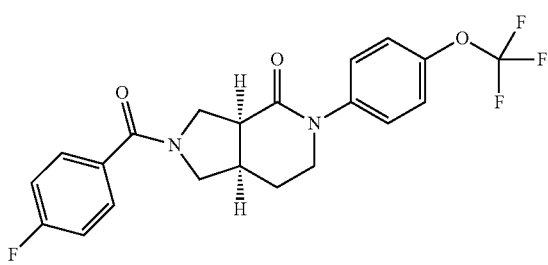 [SMILES: O=C(c1ccc(F)cc1)N1C[C@@H]2CCN(c3ccc(OC(F)(F)F)cc3)C(=O)[C@@H]2C1]

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 4-Fluoro-benzoyl chloride. $^1$H NMR (300 MHz, CDCl$_3$): δ 7.57-7.52 (m, 2H), 7.29-7.21 (m, 4H), 7.12-7.06 (m, 2H), 3.91-3.68 (m, 6H), 3.21-3.19 (m, 1H), 2.85-2.83 (m, 1H), 2.19-2.16 (m, 1H), 1.91 (bs, 1H); LC-MS: [M+1]$^+$ 423.1.

Example 4

2-(3-Methyl-butyryl)-5-(4-trifluoromethoxy-phenyl)-octahydro-pyrrolo[3,4-c]pyridin-4-one

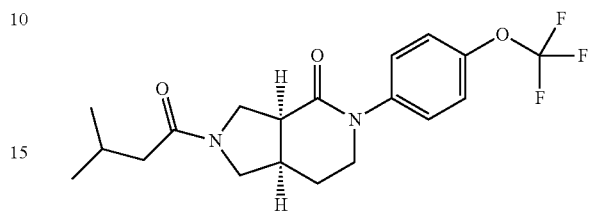

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 3-methyl-butyryl chloride. $^1$H NMR (300 MHz, CDCl$_3$): δ 7.29-7.21 (m, 4H), 3.91-3.47 (m, 6H), 3.26-3.23 (m, 1H), 2.78-2.75 (m, 1H), 2.18-1.90 (m, 5H), 0.97 (d, 6H, J=6.3 Hz); LC-MS: [M+1]+ 385.1.

Example 5

4-Oxo-5-(4-trifluoromethoxy-phenyl)-octahydro-pyrrolo[3,4-c]pyridine-2-carboxylic acid (4-trifluoromethoxy-phenyl)-amide

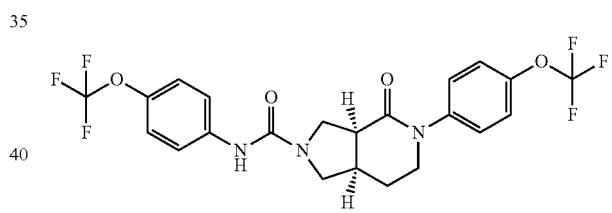

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 1-isocyanato-4-(trifluoromethoxy)benzene. $^1$H NMR (300 MHz, CDCl$_3$): δ 7.38-7.34 (m, 2H), 7.28-7.18 (m, 4H), 7.08-7.06 (m, 2H), 6.74 (s, 1H), 3.97-3.91 (t, 1H, J=9.6 Hz), 3.83-3.56 (m, 5H), 3.33-3.31 (m, 1H), 2.79-2.75 (m, 1H), 2.12-1.95 (m, 2H); LC-MS: [M+1]$^+$ 504.1.

Example 6

2-(4-Fluoro-benzyl)-5-(4-trifluoromethoxy-phenyl)-octahydro-pyrrolo[3,4-c]pyridin-4-one

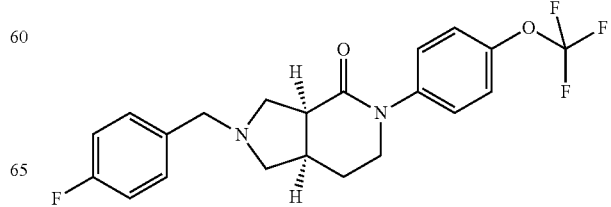

5-(4-Trifluoromethoxy-phenyl)-octahydro-pyrrolo[3,4-c]pyridin-4-one, hydrochloride (80 mg, 0.24 mmol), 1-(bromomethyl)-4-fluorobenzene (90 mg, 0.48 mmol) and Et$_3$N (0.12 g, 1.2 mmol) were added to dichloromethane (2 mL), and the mixture was stirred for 12 h. The product (30 mg, 31%) was obtained by prep-TLC (eluting with dichloromethane: MeOH=25:1). $^1$H NMR (300 MHz, CDCl$_3$): δ 7.48-7.44 (m, 2H), 7.29-7.09 (m, 6H), 4.23-4.19 (m, 2H), 3.85-3.25 (m, 7H), 2.50-2.48 (m, 1H), 2.28-2.24 (m, 1H), 1.25-1.23 (m, 1H); LC-MS: [M+1]$^+$ 409.1.

Example 7

2-(2-Chloro-benzoyl)-5-(4-trifluoromethoxy-phenyl)-octahydro-pyrrolo[3,4-c]pyridin-4-one

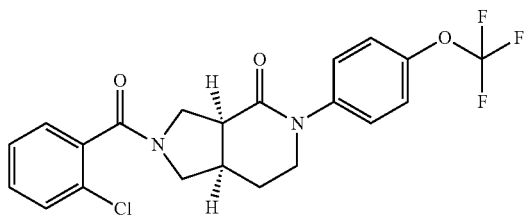 [SMILES: O=C(c1ccccc1Cl)N1C[C@@H]2CCN(c3ccc(OC(F)(F)F)cc3)C(=O)[C@@H]2C1]

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 2-Chloro-benzoyl chloride. $^1$H NMR (300 MHz, CDCl$_3$): δ 7.42-7.21 (m, 8H), 4.20-3.58 (m, 6H), 3.29-3.26 (m, 1H), 2.86-2.84 (m, 1H), 2.13-3.12 (m, 1H), 1.96-1.95 (m, 1H); LC-MS: [M+1]$^+$ 439.1.

Example 8

2-(4-Isopropyl-benzoyl)-5-(4-trifluoromethoxy-phenyl)-octahydro-pyrrolo[3,4-c]pyridin-4-one

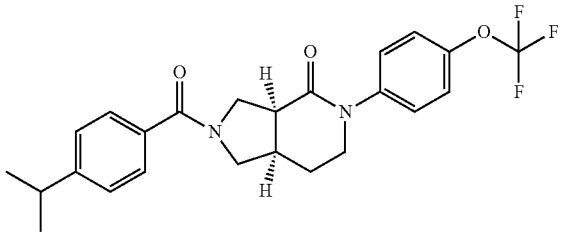 [SMILES: CC(C)c1ccc(C(=O)N2C[C@@H]3CCN(c4ccc(OC(F)(F)F)cc4)C(=O)[C@@H]3C2)cc1]

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 4-Isopropyl-benzoyl chloride. $^1$H NMR (300 MHz, CDCl$_3$): δ 7.47-7.44 (m, 2H), 7.29-7.10 (m, 6H), 3.98-3.67 (m, 6H), 3.20-3.18 (m, 1H), 2.87-2.82 (m, 2H), 2.15-1.97 (m, 2H), 1.24 (d, 6H, J=3.9 Hz); LC-MS: [M+1]$^+$ 447.2.

Example 9

2-(3-Methyl-butane-1-sulfonyl)-5-(4-trifluoromethoxy-phenyl)-octahydro-pyrrolo[3,4-c]pyridin-4-one

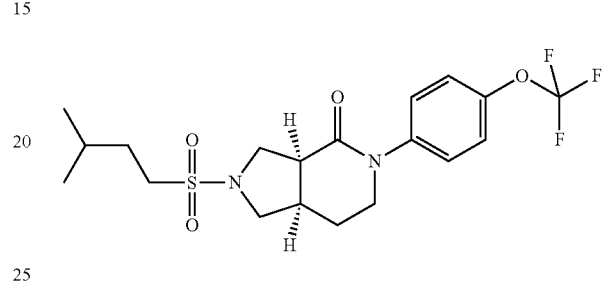

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 3-methyl-butane-1-sulfonyl chloride. $^1$H NMR (300 MHz, CDCl$_3$): δ 7.31-7.22 (m, 4H), 3.84-3.68 (m, 5H), 3.39-3.25 (m, 2H), 3.05-2.84 (m, 3H), 2.28-1.97 (m, 2H), 1.73-1.70 (m, 3H), 0.94 (d, 6H, J=6.6 Hz); LC-MS: [M+1]$^+$ 435.1.

Example 10

2-(2-Methyl-propane-1-sulfonyl)-5-(4-trifluoromethoxy-phenyl)-octahydro-pyrrolo[3,4-c]pyridin-4-one

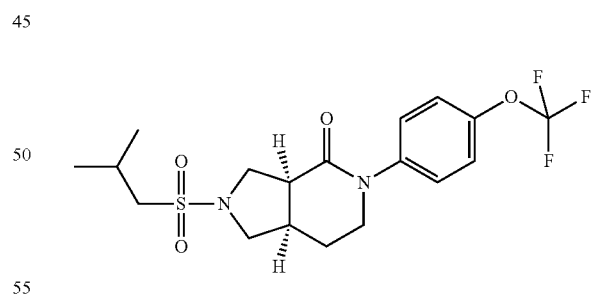

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 2-Methyl-propane-1-sulfonyl chloride. $^1$H NMR (300 MHz, CDCl$_3$): δ 7.30-7.22 (m, 4H), 3.84-3.66 (m, 5H), 3.46-3.31 (m, 2H), 2.91-2.83 (m, 3H), 2.32-2.30 (m, 1H), 2.28-1.97 (m, 2H), 1.13 (d, 6H, J=6.9 Hz); LC-MS: [M+1]$^+$ 421.1.

Example 11

2-(2-Chloro-benzenesulfonyl)-5-(4-trifluoromethoxy-phenyl)-octahydro-pyrrolo[3,4-c]pyridin-4-one

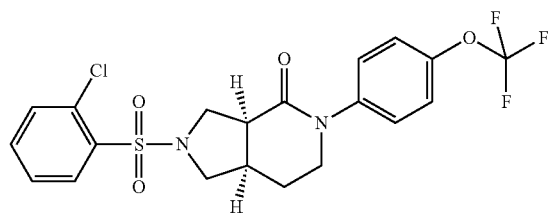 [SMILES: O=C1[C@@H]2CN(S(=O)(=O)c3ccccc3Cl)C[C@@H]2CCN1c1ccc(OC(F)(F)F)cc1]

In analogy to the procedure described for the synthesis of 2-phenylacetyl-5-(4-trifluoromethoxy-phenyl)-octahydropyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 2-Chloro-benzenesulfonyl chloride. $^1$H NMR (300 MHz, CDCl$_3$): δ 8.12-8.09 (m, 1H), 7.55-7.41 (m, 3H), 7.39-7.21 (m, 4H), 3.85-3.64 (m, 5H), 3.52-3.50 (m, 1H), 3.48-3.45 (m, 1H), 2.83-2.85 (m, 1H), 2.10-1.93 (m, 2H); LC-MS: [M+1]$^+$ 476.1.

Example 12

2-(4-Fluoro-benzenesulfonyl)-5-(4-trifluoromethoxy-phenyl)-octahydro-pyrrolo[3,4-c]pyridin-4-one

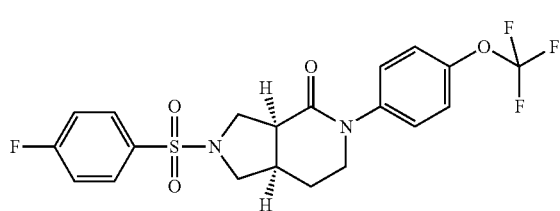 [SMILES: O=C1[C@@H]2CN(S(=O)(=O)c3ccc(F)cc3)C[C@@H]2CCN1c1ccc(OC(F)(F)F)cc1]

In analogy to the procedure described for the synthesis of 2-phenylacetyl-5-(4-trifluoromethoxy-phenyl)-octahydropyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 4-Fluoro-benzenesulfonyl chloride. $^1$H NMR (300 MHz, CDCl$_3$): δ 7.90-7.85 (m, 2H), 7.27-7.21 (m, 6H), 3.73-3.44 (m, 5H), 3.22-3.09 (m, 2H), 2.78-2.75 (m, 1H), 2.10-1.94 (m, 2H); LC-MS: [M+1]$^+$ 459.1.

Example 13

2-Phenylmethanesulfonyl-5-(4-trifluoromethoxy-phenyl)-octahydro-pyrrolo[3,4-c]pyridin-4-one

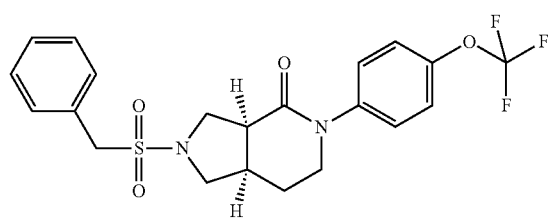 [SMILES: O=C1[C@@H]2CN(S(=O)(=O)Cc3ccccc3)C[C@@H]2CCN1c1ccc(OC(F)(F)F)cc1]

In analogy to the procedure described for the synthesis of 2-phenylacetyl-5-(4-trifluoromethoxy-phenyl)-octahydropyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and Phenyl-methanesulfonyl chloride. $^1$H NMR (300 MHz, CDCl$_3$): δ 7.43-7.25 (m, 9H), 4.31 (s, 2H), 3.74-3.64 (m, 4H), 3.36-3.34 (m, 2H), 3.17-3.07 (m, 2H), 2.00-1.84 (m, 2H); LC-MS: [M+1]$^+$ 455.1.

Example 14

4-Oxo-5-(4-trifluoromethoxy-phenyl)-octahydro-pyrrolo[3,4-c]pyridine-2-carboxylic acid (4-fluoro-phenyl)-amide

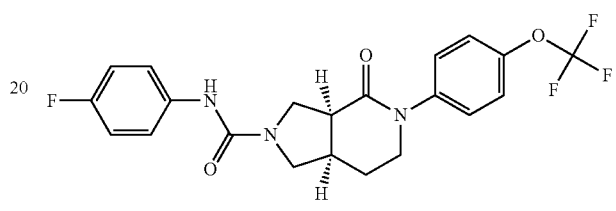

In analogy to the procedure described for the synthesis of 2-phenylacetyl-5-(4-trifluoromethoxy-phenyl)-octahydropyrrolo[3,4-c]pyridin-4-one (Example 2) the title compound was prepared from 5-(4-Trifluoromethoxy-phenyl)-octahydro-pyrrolo[3,4-c]pyridin-4-one, hydrochloride and 1-Fluoro-4-isocyanato-benzene. $^1$H NMR (300 MHz, CDCl$_3$): δ 7.34-7.21 (m, 6H), 6.98-6.57 (m, 2H), 6.36 (s, 1H), 3.96-3.28 (m, 7H), 2.82-2.79 (m, 1H), 2.15-1.93 (m, 2H); LC-MS: [M+1]$^+$ 438.1.

Example 15

2-(2-Chloro-pyridine-3-sulfonyl)-5-[4-(2,2,2-trifluoro-ethoxy)-phenyl]-octahydro-pyrrolo[3,4-c]pyridin-4-one

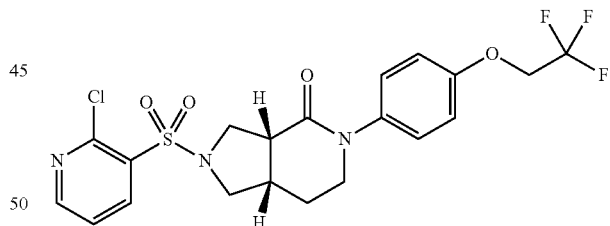

a) But-3-enyl-[4-(2,2,2-trifluoro-ethoxy)-phenyl]-amine

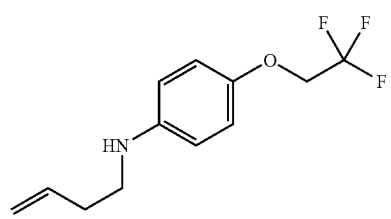 [SMILES: C=CCCNc1ccc(OCC(F)(F)F)cc1]

The mixture of 4-(2,2,2-Trifluoro-ethoxy)-phenylamine (2.5 g, 13 mmol), 4-bromobut-1-ene (3.54 g, 26 mmol) and Cs$_2$CO$_3$ (6.41 g, 20 mmol) was stirred in 30 mL of DMF at ambient temperature for 72 h. And then the mixture was filtered and washed with water. The filtrate was extracted with EtOAc (30 mL×3). The combined organic layers was washed with brine and dried with anhydrous sodium sulfate and evaporated to dryness. The residue was purified by silica-gel column chromatography (eluting with petroleum ether/ethyl acetate=30:1). The title compound (0.7 g, 22%) as brown oil was obtained. LC-MS: 246.1 [M+1]$^+$.

b) N-But-3-enyl-N-[4-(2,2,2-trifluoro-ethoxy)-phenyl]-acrylamide

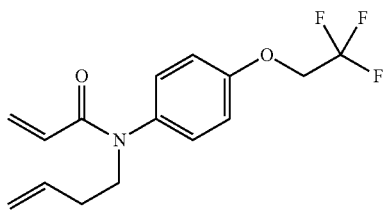 [SMILES: C=CCCN(C(=O)C=C)c1ccc(OCC(F)(F)F)cc1]

To the mixture of but-3-enyl-[4-(2,2,2-trifluoro-ethoxy)-phenyl]-amine (1.56 g, 6 mmol) and NEt$_3$ (1.7 g, 17 mmol) in 30 mL of DCM, acryloyl chloride (0.65 g, 7 mmol) was added slowly into at 0° C. The mixture was stirred at ambient temperature overnight. And then the solution was washed with water (2×15 mL) and brine (2×20 mL), dried with anhydrous sodium sulfate and evaporated to dryness. The residue was purified by silica-gel column chromatography (eluting with petroleum ether/ethyl acetate=20:1) to obtain the title compound (1.6 g, 89%) as colorless oil. LC-MS: 300.1 [M+1]$^+$.

c) 1-[4-(2,2,2-Trifluoro-ethoxy)-phenyl]-5,6-dihydro-1H-pyridin-2-one

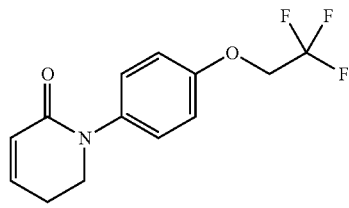 [SMILES: O=C1C=CCCN1c1ccc(OCC(F)(F)F)cc1]

A mixture of N-But-3-enyl-N-[4-(2,2,2-trifluoro-ethoxy)-phenyl]-acrylamide (1.6 g, 5 mmol) and Grubbs catalyst (0.24 g) in 30 mL of DCM was heated to 45° C. overnight. The mixture was evaporated to dryness. The residue was purified by silica-gel column chromatography (eluting with petroleum ether/ethyl acetate=5:1) to obtain the title compound as grey solid (0.9 g, 66%). LC-MS: 272.1 [M+1]$^+$.

d) 2-Benzyl-5-[4-(2,2,2-trifluoro-ethoxy)-phenyl]-octahydro-pyrrolo[3,4-c]pyridin-4-one

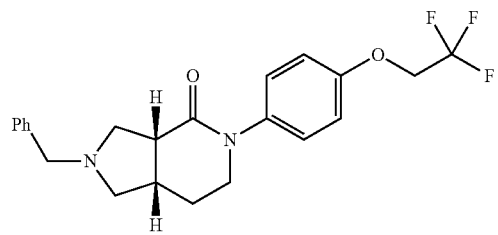 [SMILES: O=C1[C@H]2CN(Cc3ccccc3)C[C@H]2CCN1c1ccc(OCC(F)(F)F)cc1]

A mixture of 1-[4-(2,2,2-Trifluoro-ethoxy)-phenyl]-5,6-dihydro-1H-pyridin-2-one (0.27 g, 0.1 mmol), N-benzyl (methoxy)-N-((trimethylsilyl)methyl)methanamine (0.71 g, 0.3 mmol) and TFA (0.114 g, 0.1 mmol) in 20 mL of DCM was stirred at 45° C. for 30 h. The mixture was evaporated to dryness and the residue was purified by silica-gel column chromatography (eluting with petroleum ether/ethyl acetate=1:1) to obtain the title compound as colorless oil (0.125 g, 31%). LC-MS: 405.2 [M+1]$^+$.

e) 5-[4-(2,2,2-Trifluoro-ethoxy)-phenyl]-octahydro-pyrrolo[3,4-c]pyridin-4-one

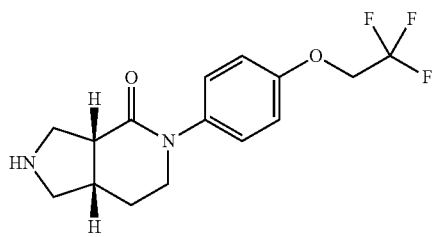 [SMILES: O=C1[C@H]2CNC[C@H]2CCN1c1ccc(OCC(F)(F)F)cc1]

The mixture of 2-Benzyl-5-[4-(2,2,2-trifluoro-ethoxy)-phenyl]-octahydro-pyrrolo[3,4-c]pyridin-4-one (2 g, 5 mmol), Pd/C (0.8 g, 20%), Boc$_2$O (2.15 g, 10 mmol) in 30 mL of MeOH was stirred at ambient temperature under hydrogen atmosphere for 3 h. The mixture was filtered and evaporated to dryness. The residue was purified by silica-gel column chromatography (eluting with DCM/MeOH=100:1) to obtain the Boc-intermediate (0.7 g, 34%) as a grey solid. LC-MS: 359.1 [M-58]$^+$. HCl (gas) was bubbled into a solution of the intermediate (0.6 g, 1 mmol) in 20 mL of EtOAc for 1.5 h and the solution was evaporated to dryness. The residue was diluted with 10 mL of EtOAc and the title compound precipitated as a white solid (0.33 g, 92%).

f) 2-(2-Chloro-pyridine-3-sulfonyl)-5-[4-(2,2,2-trifluoro-ethoxy)-phenyl]-octahydro-pyrrolo[3,4-c]pyridin-4-one In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and 2-Chloro-pyridine-3-sulfonyl chloride. $^1$H NMR (300 MHz, CD$_3$OD): δ

8.57 (dd, 1H, J=1.8 Hz), 8.45 (dd, 1H, J=1.8 Hz), 7.57 (dd, 1H, J=6 Hz), 7.20 (d, 2H, J=12 Hz), 7.04 (d, 2H, J=12 Hz), 4.58-4.50 (m, 2H), 3.84-3.62 (m, 5H), 3.48-3.44 (m, 1H), 3.36-3.21 (m, 1H), 2.90-2.85 (bs, 1H), 2.11-2.05 (m, 1H), 1.95-1.31 (m, 1H). LC-MS: 490.1 [M+1]⁺.

Example 16

2-Benzenesulfonyl-5-[4-(2,2,2-trifluoro-ethoxy)-phenyl]octahydro-pyrrolo[3,4-c]pyridin-4-one

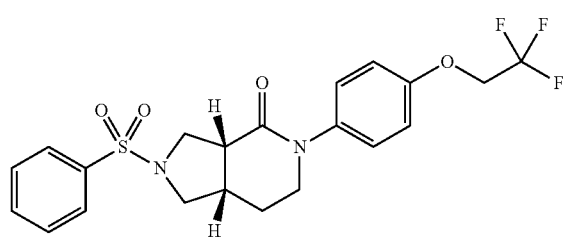 [SMILES: O=C1[C@H]2CN(S(=O)(=O)c3ccccc3)C[C@H]2CCN1c1ccc(OCC(F)(F)F)cc1]

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and Benzenesulfonyl chloride. ¹H NMR (300 MHz, CD₃OD): δ 7.90 (d, 2H, J=6 Hz), 7.76-7.64 (m, 3H), 7.15 (t, 2H, J=6 Hz), 4.59-4.51 (m, 2H), 3.74-3.45 (m, 5H), 3.26-3.21 (m, 1H), 3.05 (t, 1H, J=6 Hz), 2.77-2.71 (bs, 1H), 2.04-1.96 (m, 1H), 1.75-1.66 (m, 1H).

LC-MS: 455.1 [M+1]⁺.

Example 17

5-[4-(2,2,2-Trifluoro-ethoxy)-phenyl]-2-(2-trifluoromethoxy-benzenesulfonyl)-octahydro-pyrrolo[3,4-c]pyridin-4-one

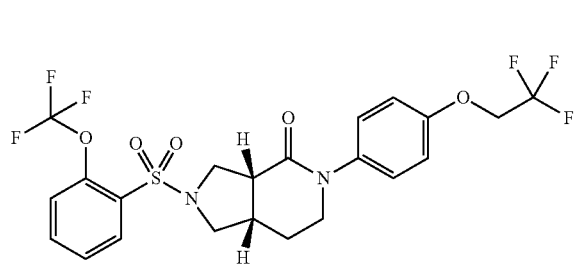 [SMILES: O=C1[C@H]2CN(S(=O)(=O)c3ccccc3OC(F)(F)F)C[C@H]2CCN1c1ccc(OCC(F)(F)F)cc1]

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and 2-Trifluoromethoxy-benzenesulfonyl chloride. ¹H NMR (300 MHz, CD₃OD): δ 8.02 (t, 1H, J=1.8 Hz), 7.79-7.73 (m, 1H), 7.54 (dd, 2H, J=3 Hz), 7.20-7.14 (m, 2H), 7.03 (dd, 2H, J=2.1 Hz), 4.57-4.49 (m, 2H), 3.78-3.55 (m, 5H), 3.38-3.31 (m, 1H), 3.21-3.13 (m, 1H), 2.76-2.82 (bs, 1H), 2.06-2.00 (m, 1H), 1.86-1.78 (m, 1H). LC-MS: 539.1 [M+1]⁺.

Example 18

2-(2-p-Tolyl-acetyl)-5-[4-(2,2,2-trifluoro-ethoxy)-phenyl]-octahydro-pyrrolo[3,4-c]pyridin-4-one

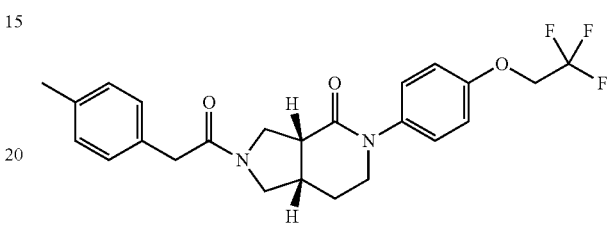

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and p-Tolyl-acetyl chloride. ¹H NMR (300 MHz, CDCl₃): δ 7.31-7.23 (m, 5H), 7.14 (dd, 2H, J=3.6 Hz), 6.93 (dd, 2H, J=4.2 Hz), 4.37-4.31 (m, 2H), 4.29-3.53 (m, 6H), 3.22-3.20 (m, 1H), 2.65-2.80 (bs, 1H), 2.04-2.02 (m, 1H), 1.86-1.85 (m, 1H). LC-MS: 433.1 [M+1]⁺.

Example 19

2-[2-(4-Fluoro-phenyl)-acetyl]-5-[4-(2,2,2-trifluoro-ethoxy)-phenyl]-octahydro-pyrrolo[3,4-c]pyridin-4-one

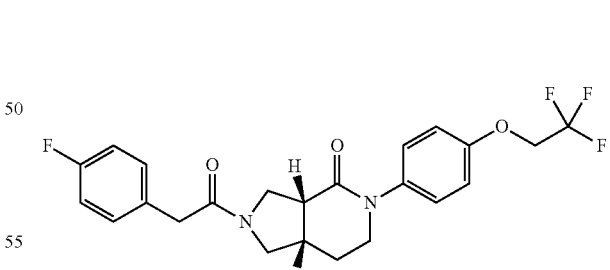

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and 2-(4-Fluoro-phenyl)-acetamide. ¹H NMR (300 MHz, CDCl₃): δ 7.25-7.12 (m, 4H), 7.02-6.91 (m, 4H), 4.33 (q, 2H, J=8.1 Hz), 3.87 (d, 2H, J=7.8 Hz), 3.94-3.50 (m, 6H), 3.26-3.10 (m, 1H), 2.80-2.68 (m, 1H), 2.11-1.70 (m, 2H). LC-MS: [M+1]⁺=451.1.

Example 20

5-[4-(2,2,2-Trifluoro-ethoxy)-phenyl]-2-(2-trifluoromethyl-benzenesulfonyl)-octahydro-pyrrolo[3,4-c]pyridin-4-one

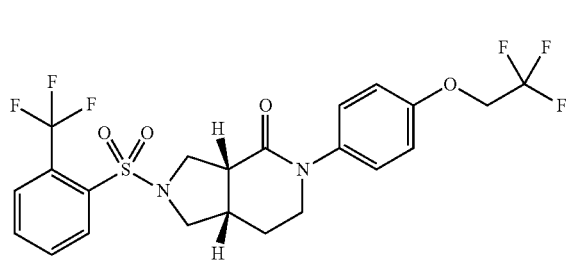 [SMILES: O=C1[C@H]2CN(S(=O)(=O)c3ccccc3C(F)(F)F)C[C@H]2CCN1c1ccc(OCC(F)(F)F)cc1]

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and 2-Trifluoromethyl-benzenesulfonyl chloride. ¹H NMR (300 MHz, CDCl₃): δ 8.16 (t, 1H, J=3.6 Hz), 7.88 (dd, 1H, J=6 Hz), 7.69 (dd, 2H, J=3 Hz), 7.14 (d, 2H, J=9 Hz), 6.93 (d, 2H, J=9 Hz), 4.36-4.28 (m, 2H), 3.76-3.58 (m, 5H), 3.42 (dd, 1H, J=1.8 Hz), 3.21-3.18 (m, 1H), 2.78-2.82 (bs, 1H), 2.03-2.01 (m, 1H), 1.95-1.91 (m, 1H). LC-MS: 523.0 [M+1]⁺.

Example 21

2-Phenylacetyl-5-[4-(2,2,2-trifluoro-ethoxy)-phenyl] octahydro-pyrrolo[3,4-c]pyridin-4-one

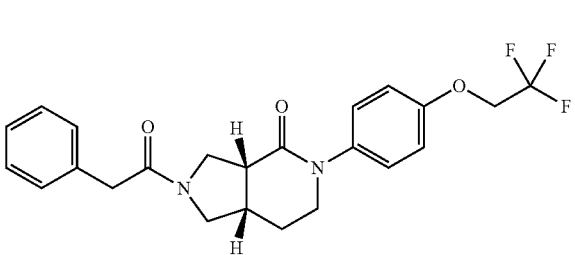 [SMILES: O=C(Cc1ccccc1)N1C[C@H]2CCN(c3ccc(OCC(F)(F)F)cc3)C(=O)[C@H]2C1]

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and phenyl-acetyl chloride. ¹H NMR (300 MHz, CDCl₃): δ 7.31-7.23 (m, 5H), 7.14 (dd, 2H, J=3.6 Hz), 6.93 (dd, 2H, J=4.2 Hz), 4.37-4.31 (m, 2H), 4.29-3.53 (m, 6H), 3.22-3.20 (m, 1H), 2.65-2.80 (bs, 1H), 2.04-2.02 (m, 1H), 1.86-1.85 (m, 1H). LC-MS: 433.1 [M+1]⁺.

Example 22

2-(3,3-Dimethyl-butyryl)-5-[4-(2,2,2-trifluoro-ethoxy)-phenyl]-octahydro-pyrrolo[3,4-c]pyridin-4-one

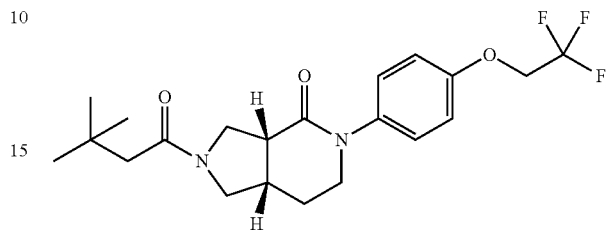

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and 3,3-Dimethyl-butyryl chloride. ¹H NMR (300 MHz, CDCl₃): δ 7.19 (d, 2H, J=9.0 Hz), 6.96 (d, 2H, J=9.0 Hz), 4.35 (q, 2H, J=7.8 Hz), 4.12-4.09 (m, 6H), 3.28-3.13 (m, 1H), 2.85-2.70 (m, 1H), 2.22 (s, 2H), 2.16-1.83 (m, 2H), 1.08 (s, 9H). LC-MS: [M+1]⁺= 413.2.

Example 23

2-(2-Chloro-benzenesulfonyl)-5-[4-(2,2,2-trifluoroethoxy)-phenyl]-octahydro-pyrrolo[3,4-c]pyridin-4-one

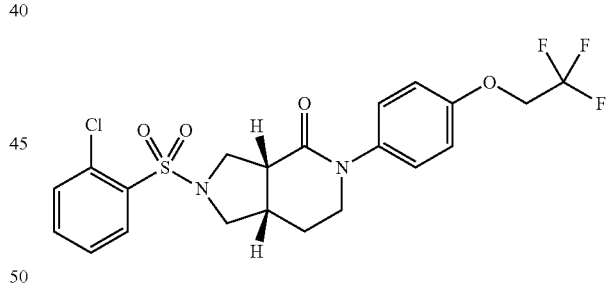

In analogy to the procedure described for the synthesis of 2-phenylacetyl-5-(4-trifluoromethoxy-phenyl)-octahydro-pyrrolo[3,4-c]pyridin-4-one (Example 2) the title compound was prepared from 5-[4-(2,2,2-Trifluoro-ethoxy)-phenyl]-octahydro-pyrrolo[3,4-c]pyridin-4-one and 2-Chloro-benzenesulfonyl chloride. ¹H NMR (300 MHz, CDCl₃): δ 8.25 (d, 1H, J=7.8 Hz), 7.70-7.53 (m, 3H), 7.32 (d, 2H, J=9.0 Hz), 7.09 (d, 2H, J=9.0 Hz), 4.48 (q, 2H, J=8.1 Hz), 3.99-3.71 (m, 5H), 3.65 (dd, 1H, $J_1$=10.2 Hz, $J_2$=3.3 Hz), 3.37 (q, 1H, J=9.0 Hz), 3.02-2.86 (m, 1H), 2.27-2.03 (m, 2H). LC-MS: [M+1]⁺= 489.1.

Example 24

N-(4-Fluoro-phenyl)-3-methyl-2-{4-oxo-5-[4-(2,2,2-trifluoro-ethoxy)-phenyl]-octahydro-pyrrolo[3,4-c]pyridin-2-yl}-butyramide

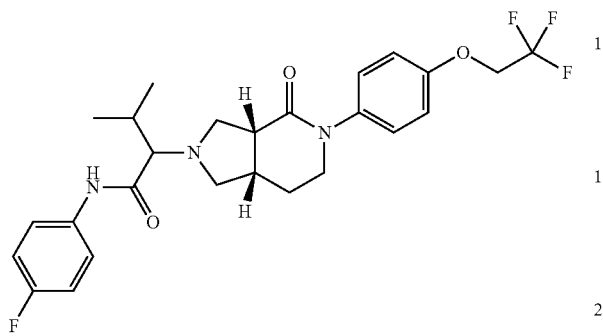

2-Bromo-3-methylbutanoic acid (2.5 g, 14 mmol) was added to 20 mL of SOCl$_2$. The mixture was refluxed for 1 h. The superfluous SOCl$_2$ was removed. The residue was added into the solution of 4-fluorobenzenamine (1.33 g, 12 mmol) in 10 mL of DCM. The mixture was stirred at ambient temperature for 0.5 h and evaporated to dryness. The crude product (3.0 g, 78%) was used in the subsequent step without further purification. A mixture of 5-[4-(2,2,2-Trifluoro-ethoxy)-phenyl]-octahydro-pyrrolo[3,4-c]pyridin-4-one (90 mg, 26 mmol), the crude α-bromoamide (211 mg, 0.77 mmol) and K$_2$CO$_3$ (106 mg, 0.77 mmol) in 15 mL of DMF was heated to 85° C. overnight. The mixture was diluted with water (15 mL) and extracted with EtOAc (2×20 mL), the combined organic layers was washed with water (2×10 mL), brine (2×10 mL), dried with anhydrous Na$_2$SO$_4$ and evaporated to dryness. The residue was purified with prep-TLC (eluting with DCM/MeOH=30:1) to obtain the title compound (33 mg, 25%) as a colorless oil. $^1$H NMR (300 MHz, CDCl$_3$): δ 7.29-7.13 (m, 2H), 7.01-6.84 (m, 4H), 6.69-6.65 (m, 2H), 6.61 (bs, 1H), 4.43-4.35 (m, 2H), 4.03-3.65 (m, 7H), 3.29-3.27 (m, 1H), 2.80 (bs, 1H), 2.10-1.65 (m, 3H), 1.11-1.07 (t, 6H, J=5.4 Hz). LC-MS: 508.2 [M+1]$^+$.

Example 25

4-Oxo-5-[4-(2,2,2-trifluoro-ethoxy)-phenyl]-octahydro-pyrrolo[3,4-c]pyridine-2-carboxylic acid tert-butyl ester

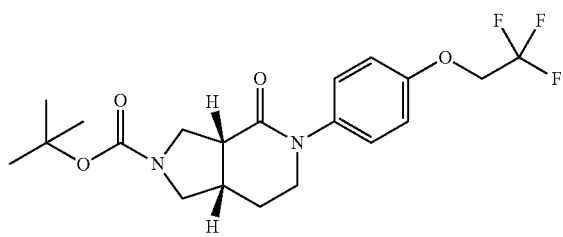 [SMILES: CC(C)(C)CC(=O)N1C[C@H]2CCN(c3ccc(OCC(F)(F)F)cc3)C(=O)[C@H]2C1]

A mixture of 2-Benzyl-5-[4-(2,2,2-trifluoro-ethoxy)-phenyl]-octahydro-pyrrolo[3,4-c]pyridin-4-one (2 g, 5 mmol), Pd/C (0.8 g, 20%), Boc$_2$O (2.15 g, 10 mmol) in 30 mL of MeOH was stirred at ambient temperature under hydrogen atmosphere for 3 h. The mixture was filtered and evaporated to dryness. The residue was purified by silica-gel column chromatography (eluting with DCM/MeOH=100:1) to obtain the title compound (0.7 g, 34%) as a grey solid.
LC-MS: 359.1 [M-58]$^+$.

Example 26

2-[2-(2,4-Dichloro-phenyl)-2-hydroxy-ethyl]-5-[4-(2,2,2-trifluoro-ethoxy)-phenyl]-octahydro-pyrrolo[3,4-c]pyridin-4-one

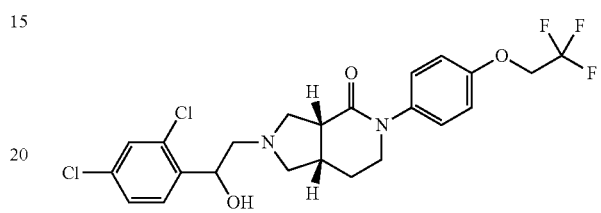

A mixture of 5-[4-(2,2,2-Trifluoro-ethoxy)-phenyl]-octahydro-pyrrolo[3,4-c]pyridin-4-one (60 mg, 0.17 mmol), 2-bromo-1-(2,4-dichlorophenyl)ethanone (92 mg, 0.34 mmol) and NEt$_3$ (80 mg, 0.8 mmol) in 20 mL of THF was stirred at ambient temperature for 4 h and evaporated to dryness. The residue was washed with water and extracted with DCM. The organic layers were washed with brine, dried with anhydrous Na$_2$SO$_4$ then evaporated to dryness. The residue was purified with prep-TLC (eluting with DCM/MeOH=10:1) to obtain the respective ketone derivative (30 mg, 35%). This was taken up in 5 mL of MeOH and NaBH$_4$ (15 mg, 0.4 mmol) was added. The mixture was stirred at ambient temperature for 2 h and evaporated to dryness. The residue was purified by prep-TLC (eluting with DCM/MeOH=10:1) to obtain the title compound (12 mg, 40%) as a colorless oil. $^1$H NMR (300 MHz, CDCl$_3$): δ 7.62 (d, 1H, J=8.4 Hz), 7.33-7.21 (m, 2H), 7.18 (d, 2H, J=3 Hz), 6.95 (d, 2H, J=7.8 Hz), 5.18 (bs, 1H), 4.34 (dd, 2H, J=7.2 Hz), 3.62 (d, 2H, J=12.9 Hz), 3.44-3.23 (m, 4H), 2.86-2.61 (m, 4H), 2.16-2.10 (m, 1H), 1.86-1.82 (m, 1H). LC-MS: 503.1 [M+1]$^+$.

Example 27

2-(2-Hydroxy-phenyl)-5-[4-(2,2,2-trifluoro-ethoxy)-phenyl]-octahydro-pyrrolo[3,4-c]pyridin-4-one

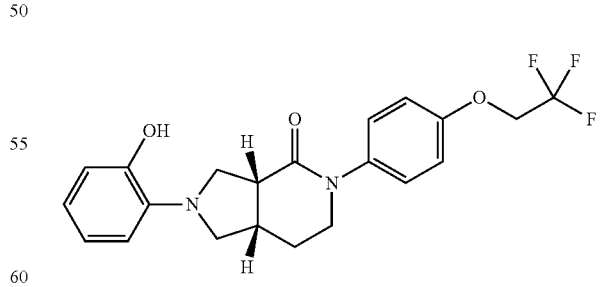

A mixture of 5-[4-(2,2,2-Trifluoro-ethoxy)-phenyl]-octahydro-pyrrolo[3,4-c]pyridin-4-one (200 mg, 0.6 mmol), 1-iodo-2-methoxybenzene (300 mg, 1.3 mmol), Pd$_2$(dba)$_3$ (100 mg, 0.1 mmol), $^t$BuOK (200 mg, 1.8 mmol) and 2-(Di-tert-butylphosphino)biphenyl (200 mg, 0.7 mmol) in toluene (20 mL) was refluxed overnight under nitrogen atmosphere.

The mixture was cooled and filtrated, the resulting solution was concentrated in vacuo. The residue was purified by silica gel column chromatography (petroleum ether/ethyl acetate=1/1) to yield the intermediate ether (30 mg, 11%). This was taken up in anhydrous dichloromethane (20 mL). The mixture was cooled to −78° C., trifluoroborane (1 mL) was added drop-wise to the mixture and the mixture was stirred at −78° C. for 2 h, 1 h at room temperature and at reflux for 1 h. The mixture was poured into water (20 mL), extracted with dichloromethane (3×20 mL), the organic layers was combined, dried over anhydrous sodium sulphate, filtrated and concentrated. The residue was purified by silica gel column chromatography (eluting with ethyl acetate/petroleum ether=½) to yield the title compound (20 mg, 69%). $^1$H NMR (300 MHz, CDCl$_3$): 7.29-7.13 (m, 4H), 7.10-6.86 (m, 5H), 4.38 (q, 2H, J=8.1 Hz), 3.79-3.26 (m, 6H), 3.08-2.92 (m, 2H), 2.27-1.92 (m, 2H). LC-MS: [M+1]$^+$=407.2.

Example 28

4-Oxo-5-(4-trifluoromethoxy-phenyl)-hexahydro-pyrrolo[3,4-c]pyrrole-2-carboxylic acid (4-trifluoromethoxy-phenyl)-amide

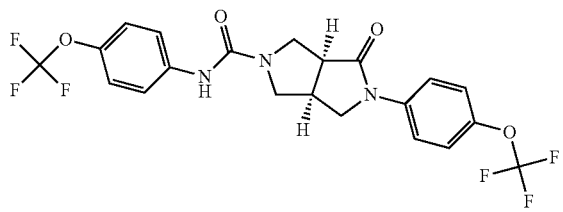 [SMILES: O=C(Nc1ccc(OC(F)(F)F)cc1)N1C[C@@H]2CN(c3ccc(OC(F)(F)F)cc3)C(=O)[C@@H]2C1]

a) 5-Benzyl-2-(4-trifluoromethoxy-phenyl)-tetrahydro-pyrrolo[3,4-c]pyrrole-1,3-dione

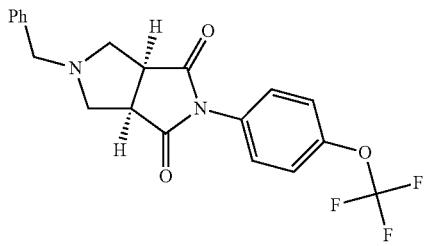 [SMILES: O=C1[C@H]2CN(Cc3ccccc3)C[C@H]2C(=O)N1c1ccc(OC(F)(F)F)cc1]

A solution of trifluoroacetic acid (0.89 g, 0.78 mmol) in dichloromethane was added at 4° C. to a stirred solution of 1-(4-(trifluoromethoxy)phenyl)-1H-pyrrole-2,5-dione (2.0 g, 7.8 mmol) and N-(methoxymethyl)(phenyl)-N-((trimethylsilyl)methyl)methanamine (2.2 g, 9.3 mmol) in dichloromethane (100 mL). After 3 h at room temperature, the solution was washed with saturated sodium bicarbonate (80 mL) and brine (80 mL) and dried over Na$_2$SO$_4$. After removal of dichloromethane, the residue was purified by column chromatography on silica gel with petroleum ether:ethyl acetate (10:1 to 5:1) to yield the title compound (2.8 g, 90%). $^1$H NMR (300 MHz, CDCl$_3$): δ 7.46-7.41 (m, 5H), 7.38-7.31 (m, 4H), 4.19 (s, 2H), 3.89-3.87 (m, 2H), 3.67-3.65 (m, 2H), 3.21 (bs, 2H), LC-MS: [M+1]$^+$ 390.9.

b) 5-Benzyl-3-hydroxy-2-(4-trifluoromethoxy-phenyl)-hexahydro-pyrrolo[3,4-c]pyrrol-1-one

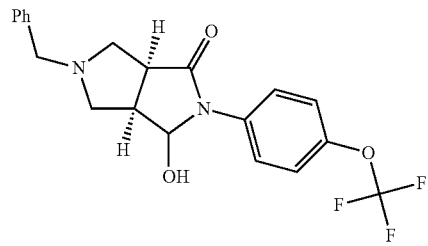 [SMILES: O=C1[C@@H]2CN(Cc3ccccc3)C[C@@H]2C(O)N1c1ccc(OC(F)(F)F)cc1]

To a cooled (−35~−40° C.) solution of 5-Benzyl-2-(4-trifluoromethoxy-phenyl)-tetrahydro-pyrrolo[3,4-c]pyrrole-1,3-dione (0.6 g, 0.5 mmol) and CeCl$_3$.7H$_2$O (0.56 g, 0.5 mmol) in 250 mL EtOH/dichloromethane (1.5:1) were sequentially added NaBH$_4$ (0.057 g, 10 mmol). The temperature was kept at −35~−40° C. for 2 h, poured into cold water (100 mL) and extracted with dichloromethane (2×80 mL). After washing the organic phase with brine (100 mL) and drying over anhydrous Na$_2$SO$_4$, the solvent was removed and the crude product was purified by column chromatography on silica gel with petroleum ether/ethyl acetate (5:1 to 2:1) to yield the title compound (0.17 g, 29%). $^1$H NMR (300 MHz, CDCl$_3$): δ 7.78 (d, 2H, J=9.0 Hz), 7.38-7.22 (m, 7H), 5.52 (d, 1H, J=6.9 Hz), 3.69 (q, 2H, J=12.6 Hz), 3.20-3.18 (m, 3H), 3.07 (bs, 1H), 2.52 (t, 1H, J=10.1 Hz), 2.31-2.28 (m, 1H); LC-MS: [M+1]$^+$ 393.0.

c) 5-Benzyl-2-(4-trifluoromethoxy-phenyl)-hexahydro-pyrrolo[3,4-c]pyrrol-1-one

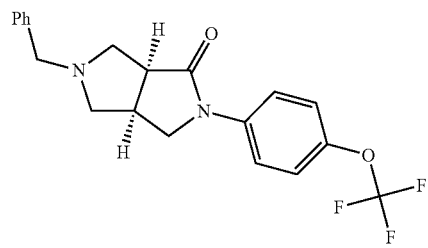 [SMILES: O=C1[C@@H]2CN(Cc3ccccc3)C[C@@H]2CN1c1ccc(OC(F)(F)F)cc1]

To a solution of 5-Benzyl-3-hydroxy-2-(4-trifluoromethoxy-phenyl)-hexahydro-pyrrolo[3,4-c]pyrrol-1-one (6.0 g, 15.3 mmol) in trifluoroacetic acid (50 mL) was added NaCNBH$_3$ (1.0 g, 15.3 mmol) and the mixture was stirred at room temperature overnight. Trifluoroacetic acid was removed by reduced pressure and the residue was added to dichloromethane (50 mL). Saturate solution of Na$_2$CO$_3$ (70 mL) was added. The mixture was extracted with dichloromethane (2×60 mL), washed with brine (100 mL), dried over Na$_2$SO$_4$. The solvent was removed and the crude product was purified by column chromatography on silica gel with petroleum ether:ethyl acetate (10:1 to 5:1) to yield the title compound (4.0 g, 70%). $^1$H NMR (300 MHz, CDCl$_3$): δ 7.73-7.69 (m, 2H), 7.31-7.22 (m, 7H), 4.04 (t, 1H, J=9.5 Hz), 3.74-3.54 (m, 3H), 3.28-3.17 (m, 2H), 2.95 (bs, 1H), 2.76-2.74 (m, 1H), 2.63-2.53 (m, 2H); LC-MS: [M+1]⁺ 376.9.

d) 4-Oxo-5-(4-trifluoromethoxy-phenyl)-hexahydro-pyrrolo[3,4-c]pyrrole-2-carboxylic acid tert-butyl ester

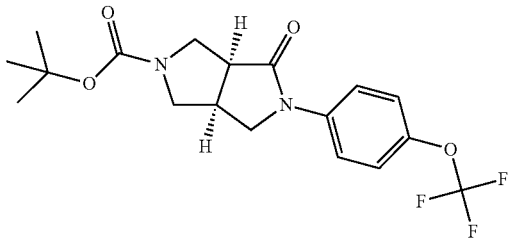 [SMILES: CC(C)(C)OC(=O)N1C[C@@H]2CN(c3ccc(OC(F)(F)F)cc3)C(=O)[C@@H]2C1]

A suspension of 5-Benzyl-2-(4-trifluoromethoxy-phenyl)-hexahydro-pyrrolo[3,4-c]pyrrol-1-one (2.5 g, 6.6 mmol), Pd/C (0.5 g, 0.1 (w/w)) and di-tert-butyldicarbonate (9.8 g, 45.5 mmol) in methanol (50 mL) was stirred under hydrogen atmosphere at room temperature overnight. The catalyst was filtered off. The filtrate was concentrated and the residue was purified by column chromatography on silica gel with petroleum ether:ethyl acetate (10:1 to 5:1) to yield the title compound (2.4 g, 94%). ¹H NMR (300 MHz, CDCl₃): δ 7.67-7.64 (m, 2H), 7.24-7.21 (m, 2H), 4.07-4.05 (m, 1H), 3.95-3.81 (m, 2H), 3.66-3.62 (m, 2H), 3.26-3.10 (m, 3H), 1.46 (s, 9H); LC-MS: [M+23]⁺ 408.9.

e) 2-(4-Trifluoromethoxy-phenyl)-hexahydro-pyrrolo[3,4-c]pyrrol-1-one, hydrochloride

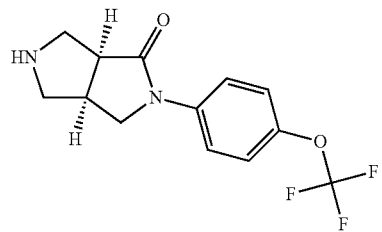 [SMILES: O=C1[C@@H]2CNC[C@@H]2CN1c1ccc(OC(F)(F)F)cc1]

To a solution of saturated hydrochloride in ethyl acetate (40 mL) was added 4-Oxo-5-(4-trifluoromethoxy-phenyl)-hexahydro-pyrrolo[3,4-c]pyrrole-2-carboxylic acid tert-butyl ester (3.0 g, 7.8 mmol) with stirring. The reaction mixture was stirred overnight. The solvent was removed under reduced pressure to yield the title compound (2.4 g, 96%). ¹H NMR (300 MHz, d₆-DMSO): δ 9.11 (bs, 1H), 7.81-7.76 (m, 2H), 7.40-7.38 (m, 2H), 4.10-4.08 (m, 1H), 3.73-3.70 (m, 1H), 3.55-3.15 (m, 6H); LC-MS: [M+1]⁺ 287.8.

f) 4-Oxo-5-(4-trifluoromethoxy-phenyl)-hexahydro-pyrrolo[3,4-c]pyrrole-2-carboxylic acid (4-trifluoromethoxy-phenyl)-amide 2-(4-Trifluoromethoxy-phenyl)-hexahydro-pyrrolo[3,4-c]pyrrol-1-one, hydrochloride (0.11 g, 0.36 mmol), 1-isocyanato-4-(trifluoromethoxy)benzene (0.15 g, 0.72 mmol) and Et₃N (0.15 g, 1.44 mmol) were added to dichloromethane (2 mL), the mixture was stirred at ambient temperature overnight. The mixture was concentrated under reduced pressure, purified by prep-HPLC to yield the title compound (50 mg, 28%) as white solid. ¹H NMR (300 MHz, CDCl₃): δ 7.68-7.65 (m, 2H), 7.42-7.40 (m, 2H), 7.39-7.13 (m, 4H), 4.18-4.03 (m, 3H), 3.79-3.69 (m, 2H), 3.45-3.38 (m, 2H), 3.22-3.20 (m, 1H); LC-MS: 489.8 [M+1]⁺.

Example 29

5-(4-Ethyl-phenyl)-4-oxo-hexahydro-pyrrolo[3,4-c]pyrrole-2-carboxylic acid (4-trifluoromethoxy-phenyl)-amide

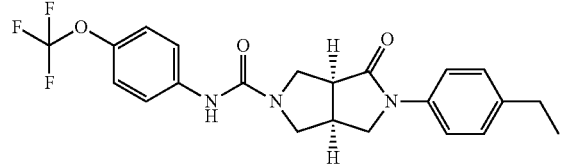 [SMILES: CCc1ccc(N2C[C@H]3CN(C(=O)Nc4ccc(OC(F)(F)F)cc4)C[C@H]3C2=O)cc1]

a) 2-(4-Ethyl-phenyl)-hexahydro-pyrrolo[3,4-c]pyrrol-1-one, hydrochloride

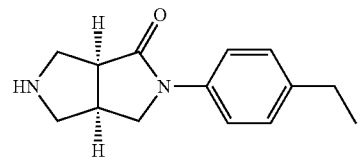 [SMILES: CCc1ccc(N2C[C@H]3CNC[C@H]3C2=O)cc1]

In analogy to the procedure described for the synthesis of 2-(4-Trifluoromethoxy-phenyl)-hexahydro-pyrrolo[3,4-c]pyrrol-1-one, hydrochloride (example 28 step e) the title compound was prepared from N-(methoxymethyl)(phenyl)-N-((trimethylsilyl)methyl)methanamine and 1-(4-(trifluoromethoxy)phenyl)-1H-pyrrole-2,5-dione with subsequent reduction and protecting group manipulation. ¹H NMR (300 MHz, CDCl₃): δ 7.54-7.51 (m, 2H), 7.20 (d, J=8.4 Hz, 2H), 4.11-4.07 (m, 1H), 3.60-3.56 (m, 2H), 3.25-3.19 (m, 3H), 2.99-2.96 (m, 2H), 2.64-2.61 (q, 2H, J=7.5 Hz), 2.39 (bs, 1H), 1.23 (t, 3H, J=7.5 Hz); LC-MS: [M+1]⁺ 231.1.

b) 5-(4-Ethyl-phenyl)-4-oxo-hexahydro-pyrrolo[3,4-c]pyrrole-2-carboxylic acid (4-trifluoromethoxy-phenyl)-amide In analogy to the procedure described for the synthesis of 4-Oxo-5-(4-trifluoromethoxy-phenyl)-hexahydro-pyrrolo[3,4-c]pyrrole-2-carboxylic acid (4-trifluoromethoxy-phenyl)-amide (Example 28, step f) the title compound was prepared from 2-(4-Ethyl-phenyl)-hexahydro-pyrrolo[3,4-c]pyrrol-1-one, hydrochloride and 1-isocyanato-4-(trifluoromethoxy)benzene. ¹H NMR (300 MHz, CDCl₃): δ 7.49 (d, 2H, J=8.1 Hz), 7.42 (d, 2H, J=9.0 Hz), 7.22 (d, 2H, J=8.4 Hz), 7.12 (d, 2H, J=8.4 Hz), 6.39 (s, 1H), 4.16-4.02 (m, 3H), 3.77-3.66 (m, 2H), 3.43-3.37 (m, 2H), 3.21-3.14 (m, 1H), 2.64 (q, 2H, J=7.5 Hz), 1.23 (t, 3H, J=7.5 Hz). LC-MS: 432.0 [M+1]⁺.

Example 30

5-Hydroxy-5-propyl-2-(4-trifluoromethoxy-phenyl)-hexahydro-cyclopenta[c]pyrrol-1-one

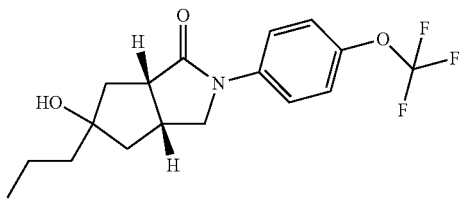 [SMILES: CCCC1(O)C[C@H]2CN(c3ccc(OC(F)(F)F)cc3)C(=O)[C@H]2C1]

a) 5-Methylene-2-(4-trifluoromethoxy-phenyl)-tetrahydro-cyclopenta[c]pyrrole-1,3-dione

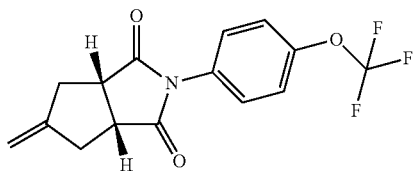 [SMILES: C=C1C[C@@H]2C(=O)N(c3ccc(OC(F)(F)F)cc3)C(=O)[C@@H]2C1]

A mixture of 5-Methylene-tetrahydro-cyclopenta[c]furan-1,3-dione (2.8 g, 18.4 mmol) and 4-(trifluoromethoxy)benzenamine (2.6 g, 14.7 mmol) was stirred at 180° C. for 0.5 h. The mixture was cooled to room temperature and purified by silica gel column (petroleum/ethyl acetate=5/1) to yield the title compound (3.0 g, 66%). ¹H NMR (300 MHz, CDCl₃): δ 7.33-7.26 (m, 4H), 4.99 (s, 2H), 3.44-3.41 (m, 2H), 2.84-2.78 (m, 4H); LC-MS: [M+1]⁺ 312.0.

b) 3-Hydroxy-5-methylene-2-(4-trifluoromethoxy-phenyl)-hexahydro-cyclopenta[c]pyrrol-1-one

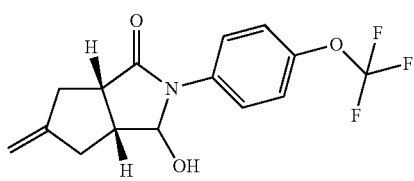 [SMILES: C=C1C[C@@H]2C(=O)N(c3ccc(OC(F)(F)F)cc3)C(O)[C@@H]2C1]

To a cooled (−20° C.) solution of 5-Methylene-2-(4-trifluoromethoxy-phenyl)-tetrahydro-cyclopenta[c]pyrrole-1,3-dione (0.7 g, 2.25 mmol) in EtOH/dichloromethane (15/10 mL) were sequentially added CeCl₃. 7H₂O (1.0 g, 2.7 mmol) and NaBH₄ (0.84 g, 22.5 mmol). The mixture was stirred for 0.5 h at −20° C., then poured into cold water (20 mL) and extracted with dichloromethane (2×15 mL). The solvent was removed by reduced pressure and the residue was purified by silica gel column (petroleum ether/ethyl acetate=5:1) to yield the title compound (0.55 g, 78%). H NMR (300 MHz, CDCl₃): δ 7.64-7.60 (m, 2H), 7.25-7.22 (m, 2H), 5.67-5.61 (m, 1H), 5.07 (s, 1H), 4.98 (s, 1H), 3.21-3.09 (m, 2H), 2.81-2.56 (m, 5H); LC-MS: [M+1]⁺ 314.1.

c) 5-Methylene-2-(4-trifluoromethoxy-phenyl)-hexahydro-cyclopenta[c]pyrrol-1-one

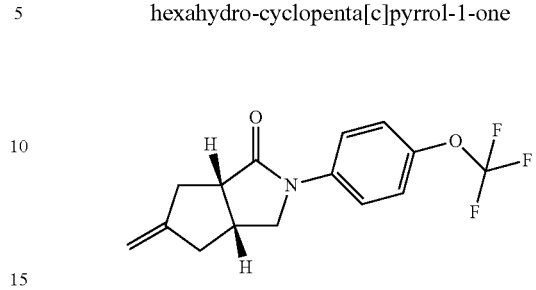

To a solution of 3-Hydroxy-5-methylene-2-(4-trifluoromethoxy-phenyl)-hexahydro-cyclopenta[c]pyrrol-1-one (0.1 g, 0.32 mmol) in trifluoroacetic acid (20 mL) was added NaCNBH₃ (0.04 g, 0.64 mmol) at −20° C., and the mixture was stirred for 1 h. Water (30 mL) was added. The mixture was extracted with dichloromethane (3×20 mL), washed with brine (50 mL), and dried over anhydrous Na₂SO₄. The solvent was removed by reduced pressure. The residue was purified by column chromatography on silica gel with petroleum ether/ethyl acetate (10:1 to 5:1) to yield the title compound (40 mg, 40%). ¹H NMR (300 MHz, CDCl₃): δ 7.69-7.64 (m, 2H), 7.25-7.19 (m, 2H), 4.91 (s, 2H), 4.07-4.01 (m, 1H), 3.54-3.49 (m, 1H), 3.19-3.12 (m, 1H), 2.96-2.71 (m, 4H), 2.25-2.18 (m, 1H); LC-MS: [M+1]⁺ 298.1.

d) 2-(4-Trifluoromethoxy-phenyl)-hexahydro-cyclopenta[c]pyrrole-1,5-dione

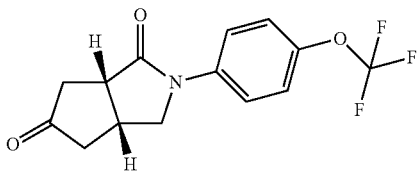 [SMILES: O=C1C[C@H]2CN(c3ccc(OC(F)(F)F)cc3)C(=O)[C@H]2C1]

A slow stream of ozone was bubbled into a solution of 5-Methylene-2-(4-trifluoromethoxy-phenyl)-hexahydro-cyclopenta[c]pyrrol-1-one (0.1 g, 0.34 mmol) in 30 mL of methylene chloride at −78° C. The stream of ozone was maintained until a slight blue color persisted. After removal of excess ozone with a stream of nitrogen, 2 mL of dimethyl sulfide was added at −78° C. The mixture was then allowed to warm to room temperature, and stirred for overnight. The solvent was removed, and the crude product was purified by prep-TLC (MeOH: dichloromethane=1:50) to yield the title compound (50 mg, 50%). ¹H NMR (300 MHz, CDCl₃): δ 7.69-7.65 (m, 2H), 7.26-7.22 (m, 2H), 4.20 (t, 1H, J=8.4 Hz), 3.69-3.66 (m, 1H), 3.45-3.38 (m, 1H), 3.22-3.16 (m, 1H), 2.88-2.56 (m, 3H), 2.25-2.18 (m, 1H); LC-MS: 300.1 [M+1]⁺.

e) 5-Hydroxy-5-propyl-2-(4-trifluoromethoxy-phenyl)-hexahydro-cyclopenta[c]pyrrol-1-one Propylmagnesium bromide (0.2 mL, 0.6 mmol, 3M) was added to a solution of 2-(4-trifluoromethoxy-phenyl)-hexahydro-cyclopenta[c]pyrrole-1,5-dione (0.1 g, 0.33 mmol) in THF (10 mL), and the mixture was stirred for 3 h at room temperature and overnight at 35° C. The solution was cooled, then poured into water (25 mL) and extracted with ether (3×20 mL), dried over Na$_2$SO$_4$. The solvent was removed and the residue was purified by prep-TLC (petroleum/ethyl acetate=1:1) to yield the title compound (25 mg, 21%). $^1$H NMR (300 MHz, CDCl$_3$): δ 7.62-7.60 (m, 2H), 7.32-7.23 (m, 2H), 4.11 (t, 1H, J=9.5 Hz), 3.71-3.67 (m, 1H), 3.18 (t, 1H, J=9.5 Hz), 2.95 (d, 1H, J=9.6 Hz), 2.25-2.21 (m, 1H), 1.98-1.88 (m, 2H), 1.81-1.76 (m, 1H), 1.61-1.34 (m, 4H), 0.95 (t, 3H, J=7.2 Hz); LC-MS: 344.2 [M+1]$^+$.

Example 31

5-Hydroxy-5-(2,2,2-trifluoro-ethoxymethyl)-2-(4-trifluoromethoxy-phenyl)-hexahydro-cyclopenta[c]pyrrol-1-one

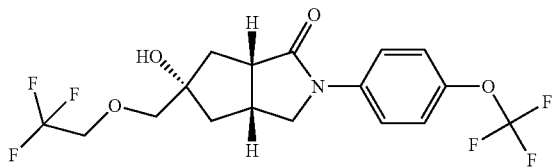 [SMILES: O=C1[C@H]2C[C@](O)(COCC(F)(F)F)C[C@H]2CN1c1ccc(OC(F)(F)F)cc1]

a) rac-(3aR,5S,6aS)-2-[4-(trifluoromethoxy)phenyl]hexahydro-1H-spiro[cyclopenta[c]pyrrole-5,2'-oxiran]-1-one and rac-(3aR,5R,6aS)-2-[4-(trifluoromethoxy)phenyl]hexahydro-1H-spiro[cyclopenta[c]pyrrole-5,2'-oxiran]-1-one

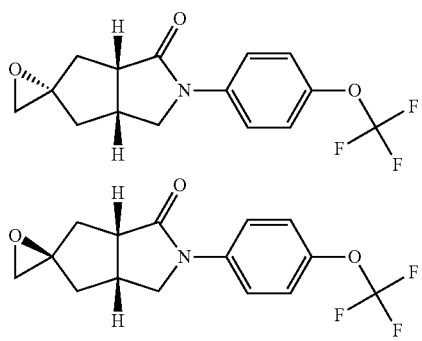

To a solution of 5-Methylene-2-(4-trifluoromethoxy-phenyl)-hexahydro-cyclopenta[c]pyrrol-1-one (0.78 g, 2.6 mmol) in dichloromethane (20 mL) was added mCPBA (0.9 g, 5.2 mmol) at 0° C., and the mixture was stirred for 6 h at room temperature. Saturated solution of NaHCO$_3$ (30 mL) was added and stirred for another 0.5 h. The mixture was extracted with dichloromethane (2×30 mL), washed with brine (60 mL) and dried over Na$_2$SO$_4$. The solvent was removed and the residue was purified by prep-TLC with petroleum ether/ethyl acetate (1:1) to yield rac-(3aR,5S,6aS)-2-[4-(trifluoromethoxy)phenyl]hexahydro-1H-spiro[cyclopenta[c]pyrrole-5,2'-oxiran]-1-one 0.11 g (13.5%) and rac-(3aR,5R,6aS)-2-[4-(trifluoromethoxy)phenyl]hexahydro-1H-spiro[cyclopenta[c]pyrrole-5,2'-oxiran]-1-one 0.27 g (33.2%). rac-(3aR,5S,6aS)-2-[4-(trifluoromethoxy)phenyl]hexahydro-1H-spiro[cyclopenta[c]pyrrole-5,2'-oxiran]-1-one: $^1$H NMR (300 MHz, CDCl$_3$): δ 7.71-7.68 (m, 2H), 7.27-7.22 (m, 2H), 4.15-4.09 (m, 1H), 3.62-3.58 (m, 1H), 3.34-3.30 (m, 1H), 3.16-3.11 (m, 1H), 2.93-2.85 (m, 2H), 2.55-2.49 (m, 1H), 2.19-1.87 (m, 3H); LC-MS: 314.0 [M+1]$^+$. rac-(3aR,5R,6aS)-2-[4-(trifluoromethoxy)phenyl]hexahydro-1H-spiro[cyclopenta[c]pyrrole-5,2'-oxiran]-1-one: $^1$H NMR (300 MHz, CDCl$_3$): δ 7.69-7.65 (m, 2H), 7.26-7.20 (m, 2H), 4.16-4.10 (m, 1H), 3.74-3.69 (m, 1H), 3.24-3.22 (m, 1H), 3.07-3.04 (m, 1H), 2.95-2.84 (m, 2H), 2.48-2.40 (m, 2H), 2.12-2.06 (m, 1H), 1.66-1.59 (m, 1H); LC-MS: 314.0 [M+1]$^+$ b) 5-Hydroxy-5-(2,2,2-trifluoro-ethoxymethyl)-2-(4-trifluoromethoxy-phenyl)-hexahydro-cyclopenta[c]pyrrol-1-one A small piece of sodium was added to 2,2,2-Trifluoroethanol (20 mL), and the mixture was stirred at 80° C. for 5 minutes, then rac-(3aR,5S,6aS)-2-[4-(trifluoromethoxy)phenyl]hexahydro-1H-spiro[cyclopenta[c]pyrrole-5,2'-oxiran]-1-one was added. The mixture was stirred for 6 h. The solution was then poured into water (25 mL) and extracted with ether (3×20 mL), dried over Na$_2$SO$_4$. The solvent was removed and the residue was purified by prep-TLC (petroleum ether:ethyl acetate=1:1) to yield the title compound. $^1$H NMR (300 MHz, CDCl$_3$): δ 7.66-7.63 (m, 2H), 7.20-7.17 (m, 2H), 4.13 (t, 1H, J=9.6 Hz), 3.86 (q, 2H, J=8.7 Hz), 3.71-3.61 (m, 3H), 3.22-3.17 (m, 1H), 3.05-2.99 (m, 1H), 2.38-2.33 (m, 1H), 2.09-1.76 (m, 4H); LC-MS: 414.1 [M+1]$^+$.

Example 32

5-Hydroxy-5-phenylaminomethyl-2-(4-trifluoromethoxy-phenyl)-hexahydro-cyclopenta[c]pyrrol-1-one

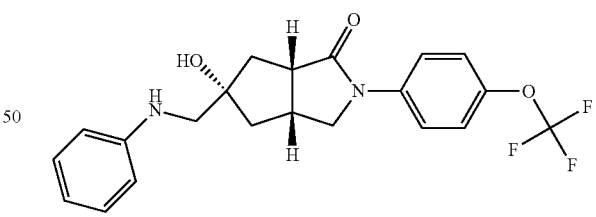

rac-(3aR,5S,6aS)-2-[4-(trifluoromethoxy)phenyl]hexahydro-1H-spiro[cyclopenta[c]pyrrole-5,2'-oxiran]-1-one (80 mg, 0.25 mmol), aniline (5 mL) and PhOH (23 mg, 0.24 mmol) were mixed together, and the mixture was stirred for 24 h at 60° C. The solution was then poured into water (25 mL) and extracted with ether (3×20 mL). The combined ether was washed with sodium hydroxide (10%, 3×10 mL), with water (30 mL) and dried over Na$_2$SO$_4$. The solvent was removed and the residue was purified by prep-TLC (petroleum ether:ethyl acetate=1:1) to yield the title compound (25 mg, 24%). $^1$H NMR (300 MHz, CDCl$_3$): δ 7.57-7.55 (m, 2H), 7.27-7.13 (m, 4H), 7.00-6.93 (m, 3H), 5.26 (bs, 1H), 4.07 (t, 1H, J=9.3 Hz), 3.75-3.73 (m, 1H), 3.34-2.22 (m, 3H), 3.05-2.90 (m, 1H), 2.46-2.42 (m, 1H), 2.02-1.90 (m, 3H); LC-MS: 407.1 [M+1]⁺.

Example 33

2-Chloro-N-[(3aR,6aS)-1-oxo-2-(4-trifluoromethoxy-phenyl)-octahydro-cyclopenta[c]pyrrol-5-yl]-benzenesulfonamide

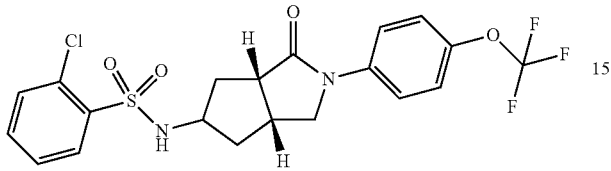

a) 5-Benzylamino-2-(4-trifluoromethoxy-phenyl)-hexahydro-cyclopenta[c]pyrrol-1-one

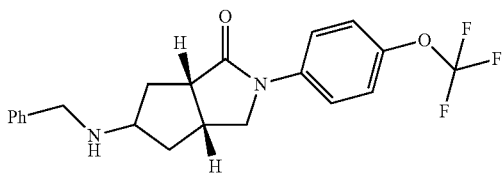 [SMILES: O=C1[C@H]2CC(NCc3ccccc3)C[C@H]2CN1c1ccc(OC(F)(F)F)cc1]

To a solution of 2-(4-Trifluoromethoxy-phenyl)-hexahydro-cyclopenta[c]pyrrole-1,5-dione (0.5 g, 1.6 mmol) and benzylamine (0.34 g, 3.2 mmol) in dichloromethane (10 mL) were added NaBH(AcO)₃ (1.0 g, 4.7 mmol). The mixture was stirred for 6 h at ambient temperature. The mixture was extracted with dichloromethane (2×15 mL), washed with brine (30 mL), dried over anhydrous Na₂SO₄. The solvent was removed, and the crude product was purified by silica column (MeOH/dichloromethane=1/30) to yield the title compound (0.4 g, 63%). ¹H NMR (300 MHz, CDCl₃): δ 7.67-7.63 (m, 2H), 7.32-7.07 (m, 7H), 4.08 (t, 1H, J=9.3 Hz), 3.76-3.56 (m, 3H), 3.34-3.31 (m, 1H), 3.16-3.09 (m, 1H), 2.88-2.83 (m, 1H), 2.21-2.02 (m, 3H), 1.65-1.58 (m, 1H).

b) 1-oxo-2-(4-trifluoromethoxy-phenyl)-octahydro-cyclopenta[c]pyrrol-5-yl]-carbamic acid tert-butyl ester

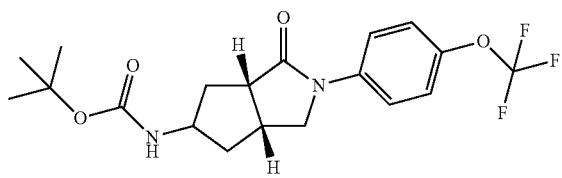 [SMILES: CC(C)(C)OC(=O)NC1C[C@H]2CN(c3ccc(OC(F)(F)F)cc3)C(=O)[C@H]2C1]

The suspension of 5-Benzylamino-2-(4-trifluoromethoxy-phenyl)-hexahydro-cyclopenta[c]pyrrol-1-one (0.4 g, 1 mmol), Pd/C (0.2 g, 0.1 (w/w)) and di-tert-butyl dicarbonate (0.45 g, 2 mmol) in methanol (30 mL) was stirred under hydrogen atmosphere at room temperature overnight. The catalyst was filtered off. The filtrate was concentrated and the residue was purified by column chromatography on silica gel with petroleum ether:ethyl acetate (10:1 to 5:1) to yield the title compound (0.22 g, 55%). ¹H NMR (300 MHz, CDCl₃): δ 7.67-7.61 (m, 2H), 7.25-7.19 (m, 2H), 4.49-4.46 (m, 1H), 4.10-3.96 (m, 1H), 3.57-3.47 (m, 1H), 3.14-3.06 (m, 1H), 2.84-2.79 (m, 1H), 2.43-2.32 (m, 2H), 1.95-1.90 (m, 1H), 1.59-1.50 (m, 1H), 1.38 (s, 9H); LC-MS: 423.1 [M+23]⁺.

c) 5-Amino-2-(4-trifluoromethoxy-phenyl)-hexahydro-cyclopenta[c]pyrrol-1-one, hydrochloride

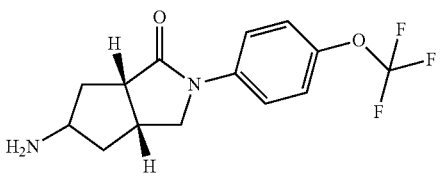 [SMILES: NC1C[C@H]2CN(c3ccc(OC(F)(F)F)cc3)C(=O)[C@H]2C1]

To a solution of saturated hydrochloride in methanol (10 mL) was added 1-Oxo-2-(4-trifluoromethoxy-phenyl)-octahydro-cyclopenta[c]pyrrol-5-yl]-carbamic acid tert-butyl Ester (0.22 g, 0.55 mmol) with stirring. The reaction mixture was stirred for 6 h. The solvent was removed under reduced pressure, then the crude product (0.2 g) was used without further purification in the consecutive step.

d) 2-Chloro-N-[(3aR,6aS)-1-oxo-2-(4-trifluoromethoxy-phenyl)-octahydro-cyclopenta[c]pyrrol-5-yl]-benzenesulfonamide 5-Amino-2-(4-trifluoromethoxy-phenyl)-hexahydro-cyclopenta[c]pyrrol-1-one, hydrochloride (60 mg, 0.18 mmol), 2-chlorobenzene-1-sulfonyl chloride (76 mg, 0.36 mmol) and Et₃N (82 mg, 0.81 mmol) were added to dichloromethane (2 mL), the mixture was stirred for overnight. The solvent was removed, and the crude product was purified by prep-TLC (petroleum ether/ethyl acetate=1:1) to yield the title compound (30 mg, 33%). ¹H NMR (300 MHz, CDCl₃): δ 8.14-8.11 (m, 1H), 7.68-7.49 (m, 5H), 7.26-7.22 (m, 2H), 5.04 (d, 1H, J=6.6 Hz), 4.05 (t, 1H, J=9.0 Hz), 3.68-3.62 (m, 2H), 3.08-3.06 (m, 1H), 2.79-2.76 (m, 1H), 2.26-2.19 (m, 2H), 1.95-1.93 (m, 1H), 1.73-1.65 (m, 1H); LC-MS: 475.0 [M+1]⁺.

Example 34

5-Hydroxy-5-phenoxymethyl-2-(4-trifluoromethoxy-phenyl)-hexahydro-cyclopenta[c]pyrrol-1-one

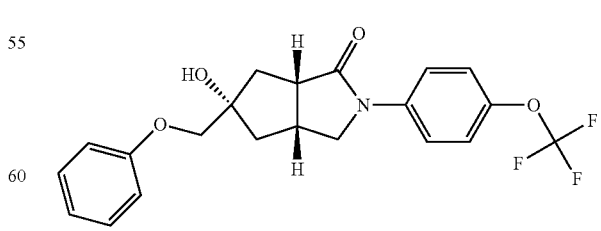

In analogy to the procedure described for the synthesis of 5-Hydroxy-5-(2,2,2-trifluoro-ethoxymethyl)-2-(4-trifluoromethoxy-phenyl)-hexahydro-cyclopenta[c]pyrrol-1-one (example 31) the title compound was prepared from rac-(3aR, 5S,6aS)-2-[4-(trifluoromethoxy)phenyl]hexahydro-1H-spiro[cyclopenta[c]pyrrole-5,2'-oxiran]-1-one and phenol. ¹H NMR (300 MHz, CDCl₃): δ 7.69-7.65 (m, 2H), 7.30-7.18 (m, 4H), 6.98-6.86 (m, 3H), 4.16 (t, 1H, J=9.3 Hz), 3.97-3.89 (m, 2H), 3.76-3.73 (m, 1H), 3.26-3.22 (m, 1H), 3.11-2.98 (m, 1H), 2.52-2.47 (m, 1H), 2.21-1.87 (m, 4H); LC-MS: 408.2 [M+1]⁺.

Example 35

5-Hydroxy-5-propoxymethyl-2-(4-trifluoromethoxy-phenyl)-hexahydro-cyclopenta[c]pyrrol-1-one

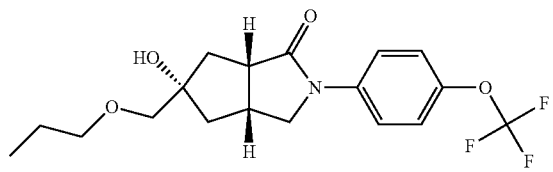 [SMILES: CCCOC[C@]1(O)C[C@H]2CN(c3ccc(OC(F)(F)F)cc3)C(=O)[C@H]2C1]

In analogy to the procedure described for the synthesis of 5-Hydroxy-5-(2,2,2-trifluoro-ethoxymethyl)-2-(4-trifluoromethoxy-phenyl)-hexahydro-cyclopenta[c]pyrrol-1-one (example 31) the title compound was prepared from rac-(3aR,5S,6aS)-2-[4-(trifluoromethoxy)phenyl]hexahydro-1H-spiro[cyclopenta[c]pyrrole-5,2'-oxiran]-1-one and propanol. ¹H NMR (300 MHz, CDCl₃): δ 7.68-7.65 (m, 2H), 7.21-7.18 (m, 2H), 4.13 (t, 1H, J=9.3 Hz), 3.73-3.69 (m, 1H), 3.46-3.39 (m, 4H), 3.23-3.20 (m, 1H), 3.17-2.98 (m, 1H), 2.38-2.20 (m, 2H), 2.06-1.56 (m, 5H), 0.94 (t, 1H, J=7.8 Hz); LC-MS: 374.1 [M+1]⁺.

Example 36

5-Butoxymethyl-5-hydroxy-2-(4-trifluoromethoxy-phenyl)-hexahydro-cyclopenta[c]pyrrol-1-one

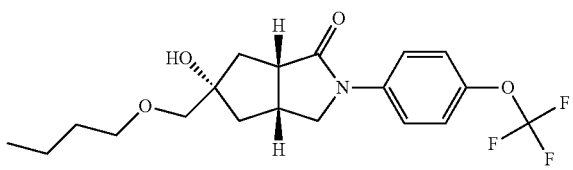 [SMILES: CCCCOC[C@]1(O)C[C@H]2CN(c3ccc(OC(F)(F)F)cc3)C(=O)[C@H]2C1]

In analogy to the procedure described for the synthesis of 5-Hydroxy-5-(2,2,2-trifluoro-ethoxymethyl)-2-(4-trifluoromethoxy-phenyl)-hexahydro-cyclopenta[c]pyrrol-1-one (example 31) the title compound was prepared from rac-(3aR,5S,6aS)-2-[4-(trifluoromethoxy)phenyl]hexahydro-1H-spiro[cyclopenta[c]pyrrole-5,2'-oxiran]-1-one and butanol. ¹H NMR (300 MHz, CDCl₃): δ 7.68-7.65 (m, 2H), 7.21-7.18 (m, 2H), 4.13 (t, 1H, J=9.3 Hz), 3.73-3.68 (m, 1H), 3.51-3.47 (m, 4H), 3.23-3.20 (m, 1H), 3.10-2.94 (m, 1H), 2.38-2.10 (m, 2H), 2.06-1.80 (m, 3H), 1.58-1.51 (m, 2H), 1.50-1.33 (m, 2H), 0.90 (t, 1H, J=6.9 Hz); LC-MS: 388.1 [M+1]⁺.

Example A

A compound of formula (I) can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:
1. A compound according to formula (I),

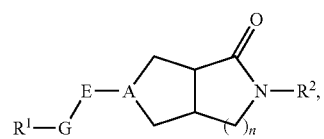

wherein:
R¹ is selected from the group consisting of alkyl, haloalkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, heteroaryl, substituted heteroaryl, heteroarylalkyl and substituted heteroarylalkyl, wherein substituted phenyl, substituted phenylalkyl, substituted phenoxyalkyl, substituted heteroaryl and substituted heteroarylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;
R² is selected from the group consisting of phenyl, substituted phenyl, heteroaryl and substituted heteroaryl, wherein substituted phenyl and substituted heteroaryl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

R³ is selected from the group consisting of hydrogen, hydroxy and alkoxy, wherein, when R³ is hydroxy or alkoxy, E is —C(R⁵R⁶)—;

R⁴ is selected from the group consisting of hydrogen, alkyl and cycloalkyl;

R⁵ is selected from the group consisting of hydrogen, alkyl and cycloalkyl;

R⁶ is selected from the group consisting of hydrogen, alkyl and cycloalkyl;

n is 1 or 2;

A is —N or —CR³;

E is a bond or —C(R⁵R⁶)—; and

G is selected from the group consisting of —O—, —NR⁴—, —CH(OH)—, —C(O)—, —C(O)O—, —C(O)NR⁴—, —S(O)₂—, —S(O)₂NR⁴— and a bond;

wherein, when both E and G are a bond, R¹ is directly attached to A, or a pharmaceutically acceptable salt thereof.

2. A compound according to claim 1, wherein R¹ is selected from the group consisting of alkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, pyridinyl, substituted pyridinyl, pyridinylalkyl and substituted pyridinylalkyl, wherein substituted phenyl, substituted phenylalkyl, substituted phenoxyalkyl, substituted pyridinyl and substituted pyridinylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl.

3. A compound according to claim 1, wherein R¹ is selected from the group consisting of alkyl, haloalkoxyalkyl, phenyl, substituted phenyl, phenylalkyl, substituted phenylalkyl and substituted pyridinyl, wherein substituted phenyl, substituted phenylalkyl and substituted pyridinyl are substituted with one to three substituents independently selected from the group consisting of alkyl, halogen, haloalkyl, hydroxy and haloalkoxy.

4. A compound according to claim 1, wherein R¹ is selected from the group consisting of alkyl, substituted phenyl and phenylalkyl, wherein substituted phenyl is substituted with one to three substituents independently selected from halogen and haloalkoxy.

5. A compound according to claim 1, wherein R¹ is alkyl.

6. A compound according to claim 1, wherein R¹ is phenylalkyl.

7. A compound according to claim 1, wherein R¹ is phenyl substituted with one to three substituents independently selected from halogen and haloalkoxy.

8. A compound according to claim 1, wherein R¹ is phenyl substituted with one or two halogen.

9. A compound according to claim 1, wherein R¹ is 2-chlorophenyl or 2,4-dichlorophenyl.

10. A compound according to claim 1, wherein R² is phenyl substituted with one substituent selected from alkyl and haloalkoxy.

11. A compound according to claim 1, wherein R² is phenyl substituted with one haloalkoxy.

12. A compound according to claim 1, wherein R² is 4-trifluoromethoxyphenyl.

13. A compound according to claim 1, wherein A is —N.

14. A compound according to claim 1, wherein A is —CR³.

15. A compound according to claim 1, wherein E is —C(R⁵R⁶)—.

16. A compound according to claim 1, wherein E is a bond.

17. A compound according to claim 1, wherein G is selected from the group consisting of O, —C(O)—, —CH(OH)— and —S(O)₂—.

18. A compound according to claim 1, wherein G is —C(O)— or —S(O)₂—.

19. A compound according to claim 1, wherein G is —S(O)₂—.

20. A compound according to claim 1, wherein R³ is hydrogen or hydroxy, wherein, when R³ is hydroxy, E is —C(R⁵R⁶)—.

21. A compound according to claim 1, wherein R³ is hydrogen.

22. A compound according to claim 1, wherein R⁴ is hydrogen.

23. A compound according to claim 1, wherein R⁵ is hydrogen or alkyl.

24. A compound according to claim 1, wherein R⁵ is hydrogen.

25. A compound according to claim 1, wherein R⁶ is hydrogen.

26. A compound according to claim 1, wherein both E and G are a bond.

27. A compound according to claim 1 wherein n is 2.

28. A compound according to claim 1, selected from the group consisting of:

(3aS,7aS)-4-oxo-5-(4-trifluoromethoxy-phenyl)-octahydro-pyrrolo[3,4-c]pyridine-2-carboxylic acid tert-butyl ester;

(3aS,7aR)-2-Phenylacetyl-5-(4-trifluoromethoxy-phenyl)-octahydro-pyrrolo[3,4-c]pyridin-4-one;

(3aS,7aR)-2-(4-Fluoro-benzoyl)-5-(4-trifluoromethoxy-phenyl)-octahydro-pyrrolo[3,4-c]pyridin-4-one;

(3aS,7aR)-2-(3-Methyl-butyryl)-5-(4-trifluoromethoxy-phenyl)-octahydro-pyrrolo[3,4-c]pyridin-4-one;

(3aS,7aR)-4-oxo-5-(4-trifluoromethoxy-phenyl)-octahydro-pyrrolo[3,4-c]pyridine-2-carboxylic acid (4-trifluoromethoxy-phenyl)-amide;

(3aS,7aR)-2-(4-Fluoro-benzyl)-5-(4-trifluoromethoxy-phenyl)-octahydro-pyrrolo[3,4-c]pyridin-4-one;

(3aS,7aR)-2-(2-Chloro-benzoyl)-5-(4-trifluoromethoxy-phenyl)-octahydro-pyrrolo[3,4-c]pyridin-4-one;

(3aS,7aR)-2-(4-Isopropyl-benzoyl)-5-(4-trifluoromethoxy-phenyl)-octahydro-pyrrolo[3,4-c]pyridin-4-one;

(3aS,7aR)-2-(3-Methyl-butane-1-sulfonyl)-5-(4-trifluoromethoxy-phenyl)-octahydro-pyrrolo[3,4-c]pyridin-4-one;

(3aS,7aR)-2-(2-Methyl-propane-1-sulfonyl)-5-(4-trifluoromethoxy-phenyl)-octahydro-pyrrolo[3,4-c]pyridin-4-one;

and pharmaceutically acceptable salts thereof.

29. A compound according to claim 1, selected from the group consisting of:

(3aS,7aR)-2-(2-Chloro-benzenesulfonyl)-5-(4-trifluoromethoxy-phenyl)-octahydro-pyrrolo[3,4-c]pyridin-4-one;

(3aS,7aR)-2-(4-Fluoro-benzenesulfonyl)-5-(4-trifluoromethoxy-phenyl)-octahydro-pyrrolo[3,4-c]pyridin-4-one;

(3aS,7aR)-2-Phenylmethanesulfonyl-5-(4-trifluoromethoxy-phenyl)-octahydro-pyrrolo[3,4-c]pyridin-4-one;

(3aS,7aR)-4-Oxo-5-(4-trifluoromethoxy-phenyl)-octahydro-pyrrolo[3,4-c]pyridine-2-carboxylic acid (4-fluorophenyl)-amide;

(3aR,7aS)-2-(2-Chloro-pyridine-3-sulfonyl)-5-[4-(2,2,2-trifluoro-ethoxy)-phenyl]-octahydro-pyrrolo[3,4-c]pyridin-4-one;

(3aR,7aS)-2-Benzenesulfonyl-5-[4-(2,2,2-trifluoro-ethoxy)-phenyl]-octahydro-pyrrolo[3,4-c]pyridin-4-one;

(3aR,7aS)-5-[4-(2,2,2-Trifluoro-ethoxy)-phenyl]-2-(2-trifluoromethoxy-benzenesulfonyl)-octahydro-pyrrolo[3,4-c]pyridin-4-one;

(3aR,7aS)-2-(2-p-Tolyl-acetyl)-5-[4-(2,2,2-trifluoro-ethoxy)-phenyl]-octahydro-pyrrolo[3,4-c]pyridin-4-one;

(3aR,7aS)-2-[2-(4-Fluoro-phenyl)-acetyl]-5-[4-(2,2,2-trifluoro-ethoxy)-phenyl]-octahydro-pyrrolo[3,4-c]pyridin-4-one;

(3aR,7aS)-5-[4-(2,2,2-Trifluoro-ethoxy)-phenyl]-2-(2-trifluoromethyl-benzenesulfonyl)-octahydro-pyrrolo[3,4-c]pyridin-4-one;

and pharmaceutically acceptable salts thereof.

30. A compound according to claim 1, selected from the group consisting of:

(3aR,7aS)-2-Phenylacetyl-5-[4-(2,2,2-trifluoro-ethoxy)-phenyl]-octahydro-pyrrolo[3,4-c]pyridin-4-one;

3aR,7aS)-2-(3,3-Dimethyl-butyryl)-5-[4-(2,2,2-trifluoro-ethoxy)-phenyl]-octahydro-pyrrolo[3,4-c]pyridin-4-one;

(3aR,7aS)-2-(2-Chloro-benzenesulfonyl)-5-[4-(2,2,2-trifluoro-ethoxy)-phenyl]-octahydro-pyrrolo[3,4-c]pyridin-4-one;

N-(4-Fluoro-phenyl)-3-methyl-2-{(3aR,7aS)-4-oxo-5-[4-(2,2,2-trifluoro-ethoxy)-phenyl]-octahydro-pyrrolo[3,4-c]pyridin-2-yl}-butyramide;

(3aR,7aS)-4-oxo-5-[4-(2,2,2-trifluoro-ethoxy)-phenyl]-octahydro-pyrrolo[3,4-c]pyridine-2-carboxylic acid tert-butyl ester;

(3aR,7aS)-2-[2-(2,4-Dichloro-phenyl)-2-hydroxy-ethyl]-5-[4-(2,2,2-trifluoro-ethoxy)-phenyl]-octahydro-pyrrolo[3,4-c]pyridin-4-one;

(3aR,7aS)-2-(2-Hydroxy-phenyl)-5-[4-(2,2,2-trifluoro-ethoxy)-phenyl]-octahydro-pyrrolo[3,4-c]pyridin-4-one;

(3aR,6aS)-4-oxo-5-(4-trifluoromethoxy-phenyl)-hexahydro-pyrrolo[3,4-c]pyrrole-2-carboxylic acid (4-trifluoromethoxy-phenyl)-amide;

(3aR,6aS)-5-(4-Ethyl-phenyl)-4-oxo-hexahydro-pyrrolo[3,4-c]pyrrole-2-carboxylic acid (4-trifluoromethoxy-phenyl)-amide;

(3aR,6aS)-5-Hydroxy-5-propyl-2-(4-trifluoromethoxy-phenyl)-hexahydro-cyclopenta[c]pyrrol-1-one;

and pharmaceutically acceptable salts thereof.

31. A compound according to claim 1, selected from the group consisting of:

(3aR,5S,6aS)-5-Hydroxy-5-(2,2,2-trifluoro-ethoxymethyl)-2-(4-trifluoromethoxy-phenyl)-hexahydro-cyclopenta[c]pyrrol-1-one;

(3aR,6aS)-5-Hydroxy-5-phenylaminomethyl-2-(4-trifluoromethoxy-phenyl)-hexahydro-cyclopenta[c]pyrrol-1-one;

2-Chloro-N-[(3aR,6aS)-1-oxo-2-(4-trifluoromethoxy-phenyl)-octahydro-cyclopenta[c]pyrrol-5-yl]-benzenesulfonamide;

(3aR,5S,6aS)-5-Hydroxy-5-phenoxymethyl-2-(4-trifluoromethoxy-phenyl)-hexahydro-cyclopenta[c]pyrrol-1-one;

(3aR,5S,6aS)-5-Hydroxy-5-propoxymethyl-2-(4-trifluoromethoxy-phenyl)-hexahydro-cyclopenta[c]pyrrol-1-one;

(3aR,5S,6aS)-5-Butoxymethyl-5-hydroxy-2-(4-trifluoromethoxy-phenyl)-hexahydro-cyclopenta[c]pyrrol-1-one;

and pharmaceutically acceptable salts thereof.

32. A compound according to claim 1, selected from (3aS,7aR)-2-Phenylacetyl-5-(4-trifluoromethoxy-phenyl)-octahydro-pyrrolo[3,4-c]pyridin-4-one;

(3aS,7aR)-2-(2-Chloro-benzenesulfonyl)-5-(4-trifluoromethoxy-phenyl)-octahydro-pyrrolo[3,4-c]pyridin-4-one;

(3aR,7aS)-5-[4-(2,2,2-Trifluoro-ethoxy)-phenyl]-2-(2-trifluoromethoxy-benzenesulfonyl)-octahydro-pyrrolo[3,4-c]pyridin-4-one;

(3aR,7aS)-2-[2-(2,4-Dichloro-phenyl)-2-hydroxy-ethyl]-5-[4-(2,2,2-trifluoro-ethoxy)-phenyl]-octahydro-pyrrolo[3,4-c]pyridin-4-one;

(3aR,5S,6aS)-5-Butoxymethyl-5-hydroxy-2-(4-trifluoromethoxy-phenyl)-hexahydro-cyclopenta[c]pyrrol-1-one;

and pharmaceutically acceptable salts thereof.

33. A pharmaceutical composition comprising a compound in according to claim 1 and a therapeutically inert carrier.

* * * * *